US007138276B2

(12) United States Patent
Sakano et al.

(10) Patent No.: US 7,138,276 B2
(45) Date of Patent: Nov. 21, 2006

(54) DIFFERENTIATION-SUPPRESSIVE POLYPEPTIDE SERRATE-2 AND METHODS OF USE

(75) Inventors: Seiji Sakano, Shizuoka (JP); Akira Itoh, Shizuoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 566 days.

(21) Appl. No.: 10/219,248

(22) Filed: Aug. 16, 2002

(65) Prior Publication Data
US 2003/0022368 A1 Jan. 30, 2003

Related U.S. Application Data

(62) Division of application No. 09/855,722, filed on May 16, 2001, now Pat. No. 6,638,741, which is a division of application No. 09/214,278, filed as application No. PCT/JP97/02414 on Jul. 11, 1997, now Pat. No. 6,291,210.

(30) Foreign Application Priority Data

| Jul. 16, 1996 | (JP) | ................................. 8-186220 |
| May 14, 1997 | (JP) | ................................. 9-124063 |

(51) Int. Cl.
C12N 5/08 (2006.01)
A61K 38/18 (2006.01)

(52) U.S. Cl. ........................................ 435/377; 530/350
(58) Field of Classification Search ..................... None
See application file for complete search history.

(56) References Cited

U.S. PATENT DOCUMENTS 4,603,106 A 7/1986 Cerami et al.
6,004,924 A * 12/1999 Ish-Horowicz et al. ......... 514/2

FOREIGN PATENT DOCUMENTS

| WO | WO 92/19734 | 11/1992 |
| WO | WO 96/02645 | 2/1996 |
| WO | WO 96/11212 | 4/1996 |
| WO | WO 96/27610 | 9/1996 |
| WO | WO 97/19172 | 5/1997 |
| WO | WO 98/58958 | 12/1998 |

OTHER PUBLICATIONS

Michael L. Deftos et al., "Notch signaling in T cell development", Current Opinion in Immunology, vol. 12, No. 2, Apr. 1, 2000, pp. 166-172.
R.S. Mann et al., "Homo sapiens Jagged 2 mRNA, complete cds.", Jun. 21, 1997, Database Accession No. HSAF3521, XP-002272654.
S. Sakano et al., "Human notch ligands affect both hematopoietic progenitor and long term-culture initiating cells (LTC-IC) in in vitro culture", Nov. 15, 1997, Database Accession No. PREV199800067058, XP-002272655.

S. Artavanis-Tsakonas et al., "Notch Signaling", pp. 225-232, Science, vol. 268, Apr. 14, 1995.
John E. Wagner et al., "Isolation of Small, Primitive Human Hematopoietic Stem Cells: Distribution of Cell Surface Cytokine Receptors and Growth in SCID-Hu Mice", pp. 512-523, Blood, vol. 86, No. 2, Jul. 15, 1995.
L.W. Ellisen et al., "TAN-1, the Human Homolog of the Drosophila Notch Gene, Is Broken by Chromosomal Trans-locations in T Lymphoblastic Neoplasms", pp. 649-661, Cell, vol. 66, Aug. 23, 1991.
L.A. Milner et al., "A Human Homologue of the Drosophila Developmental Gene, Notch, Is Expressed in CD34+ Hematopoietic Precursors", pp. 2057-2062, Blood, vol. 83, No. 8, Apr. 15, 1994.
R.G. Fehon et al., "Molecular Interactions between the Protein Products of the Neurogenic Loci Notch and Delta, Two EGF-Homologous Genes in Drosophila", pp. 523-534, Cell, vol. 61, May 4, 1990.
I. Rebay et al., "Specific EGF Repeats of Notch Mediate Interactions with Delta and Serrate: Implications for Notch as a Multifuctional Receptor", pp. 687-699, Cell, vol. 67, Nov. 15, 1991.
R.W. Jackman et al., "Characterization of a thrombomodulin cDNA reveals structural similarity to the low density lipoprotein receptor", pp. 8834-8838, Proc. Natl. Acad, Sci. USA, vol. 83, Dec. 1986.
D.W. Russell et al., "Domain Map of the LDL Receptor: Sequence Homology with the Epidermal Growth Factor Precur-sor", pp. 577-585, Cell, vol. 37, 1984.
B. Furie et al., "The Molecular Basis of Blood Coagula-tion", pp. 505-518, Cell, vol. 53, May 20, 1988.
J. Sambrook et al., "Molecular Cloning" A Laboratory Manual, Second Edition, two pages, Cold Spring Harbor Laboratory Press, 1989.
The Genome Directory, Supplement to Nature, vol. 377, Issue No. 6547S, Sep. 28, 1995.
J. Kyte et al., "A Simple Method for Displaying the Hydro-pathic Character of a Protein", pp. 105-132, J. Mol. Biol. vol. 157, 1982.
L. Enquist et al., "In Vitro Packaging of \ Dam Vectors and Their Use in Cloning DNA Fragments", pp. 281-299, Methods in Enzymology, vol. 68, 1979.
K. Fitzgerald et al., "Interchangeability of Caenorhab-ditis elegans DSL proteins and intrinsic signalling activity of their extracellular domains in vivo", pp. 4275-4282, Development, vol. 121, Sep. 13, 1995.
T. Yokota et al., "Introduction and expression of gene and its analysis method", eight pages, Independent Volume of Experimental Medicine Bio Manual Series 4, Apr. 20, 1994.

(Continued)

Primary Examiner—Eileen B. O'Hara
(74) Attorney, Agent, or Firm—Young & Thompson

(57) ABSTRACT

A novel human serrate-2 polypeptide consisting of a polypeptide containing the amino acid sequence described in SEQ ID NO:1 in the Sequence Listing and having the effect of regulating the differentiation of undifferentiated cells involving stem cells; its gene; a process for producing the same; and an antibody specifically recognizing the polypeptide.

12 Claims, No Drawings

OTHER PUBLICATIONS

J. Folkman et al., "Angiogenic Factors", pp. 442-447, Science, vol. 235, Jan. 23, 1987.

E. Harlow et al., "Antibodies" A Laboratory Manual, ten pages, Cold Spring Harbor Laboratory, 1988.

Translation of "Stem Cell which is continuing division with self-replication activity", twelve pages, 1996.

G. Zettlmeissl et al., "Expression and Characterization of Human CD4: Immunoglobulin Fusion Proteins", pp. 347-353, DNA and Cell Biology, vol. 9, No. 5, 1990.

E.A. Kabat et al., "Sequence of Proteins of Immunological Interest", nine pages, U.S. Department of Health and Human Services, 1991.

H. J. Sutherland et al., "Characterization and Partial Purification of Human Marrow Cells Capable of Initiating Long-Term Hematopoiesis In Vitro", pp. 1563-1570, Blood, vol. 74, No. 5, Oct. 1989.

H. J. Sutherland et al., "Functional characterization of individual human hematopoietic stem cells cultured at limiting dilution on supportive marrow stromal layers.", pp. 3584-3588, Proc. Natl. Acad. Sci. USA, vol. 87, May 1990.

C. Taswell, "Limiting Dilution Assays for the Determination of Immunocompetent Cell Frequencies", pp. 1614-1619, The Journal of Immunology, vol. 126, No. 4, Apr. 1981.

E. Borenfreund et al., A Simple Quantitative Procedure Using Monolayer Cultures For Cytotoxicity Assays (HTD/NR-90) pp. 7-9, Journal of Tissue Culture Methods, vol. 9, No. 1, 1984.

D. Henrique et al., "Expression of a Delta homologue in prospective neurons in the chick", pp. 787-790, Nature, vol. 375, Jun. 29, 1995.

A. Chitnis et al., "Primary neurogenesis in Xenopus embry-os regulated by a homologue of the *Drosophila neurogenic* gene Delta", pp. 761-766, Nature, vol. 375, Jun. 29, 1995.

C.E. Lindsell et al., "Jagged: A Mammalian Ligand That Activates Notch1", pp. 909-917, Cell, vol. 80, Mar. 24, 1995.

* cited by examiner

```
                             SEQUENCE LISTING

<160> NUMBER OF SEQ ID NOS: 32

<210> SEQ ID NO 1
    <211> LENGTH: 214
    <212> TYPE: PRT
    <213> ORGANISM: Homo sapiens

<400> SEQUENCE: 1

Met Gly Tyr Phe Glu Leu Gln Leu Ser Ala Leu Arg Asn Val Asn Gly
     1               5                  10                  15

Glu Leu Leu Ser Gly Ala Cys Cys Asp Gly Asp Gly Arg Thr Thr Arg
                    20                  25                  30

Ala Gly Gly Cys Gly His Asp Glu Cys Asp Thr Tyr Val Arg Val Cys
                35                  40                  45

Leu Lys Glu Tyr Gln Ala Lys Val Thr Pro Thr Gly Pro Cys Ser Tyr
        50                  55                  60

Gly His Gly Ala Thr Pro Val Leu Gly Gly Asn Ser Phe Tyr Leu Pro
     65                  70                  75                  80

Pro Ala Gly Ala Ala Gly Asp Arg Ala Arg Ala Arg Ala Arg Ala Gly
                    85                  90                  95

Gly Asp Gln Asp Pro Gly Leu Val Val Ile Pro Phe Gln Phe Ala Trp
                100                 105                 110

Pro Arg Ser Phe Thr Leu Ile Val Glu Ala Trp Asp Trp Asp Asn Asp
                115                 120                 125

Thr Thr Pro Asn Glu Glu Leu Leu Ile Glu Arg Val Ser His Ala Gly
            130                 135                 140

Met Ile Asn Pro Glu Asp Arg Trp Lys Ser Leu His Phe Ser Gly His
    145                 150                 155                 160

Val Ala His Leu Glu Leu Gln Ile Arg Val Arg Cys Asp Glu Asn Tyr
                    165                 170                 175

Tyr Ser Ala Thr Cys Asn Lys Phe Cys Arg Pro Arg Asn Asp Phe Phe
                180                 185                 190

Gly His Tyr Thr Cys Asp Gln Tyr Gly Asn Lys Ala Cys Met Asp Gly
                195                 200                 205

Trp Met Gly Lys Glu Cys
        210

<210> SEQ ID NO 2
    <211> LENGTH: 1055
    <212> TYPE: PRT
    <213> ORGANISM: Homo sapiens

<400> SEQUENCE: 2

Met Gly Tyr Phe Glu Leu Gln Leu Ser Ala Leu Arg Asn Val Asn Gly
     1               5                  10                  15

Glu Leu Leu Ser Gly Ala Cys Cys Asp Gly Asp Gly Arg Thr Thr Arg
                    20                  25                  30

Ala Gly Gly Cys Gly His Asp Glu Cys Asp Thr Tyr Val Arg Val Cys
                35                  40                  45
```

```
Leu Lys Glu Tyr Gln Ala Lys Val Thr Pro Thr Gly Pro Cys Ser Tyr
 50                  55                  60

Gly His Gly Ala Thr Pro Val Leu Gly Gly Asn Ser Phe Tyr Leu Pro
 65                  70                  75                  80

Pro Ala Gly Ala Ala Gly Asp Arg Ala Arg Ala Arg Ala Gly
                 85                  90                  95

Gly Asp Gln Asp Pro Gly Leu Val Val Ile Pro Phe Gln Phe Ala Trp
                100                 105                 110

Pro Arg Ser Phe Thr Leu Ile Val Glu Ala Trp Asp Trp Asp Asn Asp
            115                 120                 125

Thr Thr Pro Asn Glu Glu Leu Leu Ile Glu Arg Val Ser His Ala Gly
        130                 135                 140

Met Ile Asn Pro Glu Asp Arg Trp Lys Ser Leu His Phe Ser Gly His
145                 150                 155                 160

Val Ala His Leu Glu Leu Gln Ile Arg Val Arg Cys Asp Glu Asn Tyr
                165                 170                 175

Tyr Ser Ala Thr Cys Asn Lys Phe Cys Arg Pro Arg Asn Asp Phe Phe
            180                 185                 190

Gly His Tyr Thr Cys Asp Gln Tyr Gly Asn Lys Ala Cys Met Asp Gly
        195                 200                 205

Trp Met Gly Lys Glu Cys Lys Glu Ala Val Cys Lys Gln Gly Cys Asn
210                 215                 220

Leu Leu His Gly Gly Cys Thr Val Pro Gly Glu Cys Arg Cys Ser Tyr
225                 230                 235                 240

Gly Trp Gln Gly Arg Phe Cys Asp Glu Cys Val Pro Tyr Pro Gly Cys
                245                 250                 255

Val His Gly Ser Cys Val Glu Pro Trp Gln Cys Asn Cys Glu Thr Asn
            260                 265                 270

Trp Gly Gly Leu Leu Cys Asp Lys Asp Leu Asn Tyr Cys Glu Ser His
        275                 280                 285

His Pro Cys Thr Asn Gly Gly Thr Cys Ile Asn Ala Glu Pro Asp Gln
290                 295                 300

Tyr Arg Cys Thr Cys Pro Asp Gly Tyr Ser Gly Arg Asn Cys Glu Lys
305                 310                 315                 320

Ala Glu His Ala Cys Thr Ser Asn Pro Cys Ala Asn Gly Gly Ser Cys
                325                 330                 335

His Glu Val Pro Ser Gly Phe Glu Cys His Cys Pro Ser Gly Trp Ser
            340                 345                 350

Gly Pro Thr Cys Ala Leu Asp Ile Asp Glu Cys Ala Ser Asn Pro Cys
        355                 360                 365

Ala Ala Gly Gly Thr Cys Val Asp Gln Val Asp Gly Phe Glu Cys Ile
        370                 375                 380

Cys Pro Glu Gln Trp Val Gly Ala Thr Cys Gln Leu Asp Ala Asn Glu
385                 390                 395                 400

Cys Glu Gly Lys Pro Cys Leu Asn Ala Phe Ser Cys Lys Asn Leu Ile
                405                 410                 415

Gly Gly Tyr Tyr Cys Asp Cys Ile Pro Gly Trp Lys Gly Ile Asn Cys
            420                 425                 430

His Ile Asn Val Asn Asp Cys Arg Gly Gln Cys Gln His Gly Gly Thr
        435                 440                 445

Cys Lys Asp Leu Val Asn Gly Tyr Gln Cys Val Cys Pro Arg Gly Phe
450                 455                 460
```

-continued

```
Gly Gly Arg His Cys Glu Leu Glu Arg Asp Lys Cys Ala Ser Ser Pro
465                 470                 475                 480

Cys His Ser Gly Gly Leu Cys Glu Asp Leu Ala Asp Gly Phe His Cys
            485                 490                 495

His Cys Pro Gln Gly Phe Ser Gly Pro Leu Cys Glu Val Asp Val Asp
        500                 505                 510

Leu Cys Glu Pro Ser Pro Cys Arg Asn Gly Ala Arg Cys Tyr Asn Leu
    515                 520                 525

Glu Gly Asp Tyr Tyr Cys Ala Cys Pro Asp Asp Phe Gly Gly Lys Asn
530                 535                 540

Cys Ser Val Pro Arg Glu Pro Cys Pro Gly Gly Ala Cys Arg Val Ile
545                 550                 555                 560

Asp Gly Cys Gly Ser Asp Ala Gly Pro Gly Met Pro Gly Thr Ala Ala
            565                 570                 575

Ser Gly Val Cys Gly Pro His Gly Arg Cys Val Ser Gln Pro Gly Gly
        580                 585                 590

Asn Phe Ser Cys Ile Cys Asp Ser Gly Phe Thr Gly Thr Tyr Cys His
    595                 600                 605

Glu Asn Ile Asp Asp Cys Leu Gly Gln Pro Cys Arg Asn Gly Gly Thr
610                 615                 620

Cys Ile Asp Glu Val Asp Ala Phe Arg Cys Phe Cys Pro Ser Gly Trp
625                 630                 635                 640

Glu Gly Glu Leu Cys Asp Thr Asn Pro Asn Asp Cys Leu Pro Asp Pro
            645                 650                 655

Cys His Ser Arg Gly Arg Cys Tyr Asp Leu Val Asn Asp Phe Tyr Cys
        660                 665                 670

Ala Cys Asp Asp Gly Trp Lys Gly Lys Thr Cys His Ser Arg Glu Phe
    675                 680                 685

Gln Cys Asp Ala Tyr Thr Cys Ser Asn Gly Gly Thr Cys Tyr Asp Ser
690                 695                 700

Gly Asp Thr Phe Arg Cys Ala Cys Pro Pro Gly Trp Lys Gly Ser Thr
705                 710                 715                 720

Cys Ala Val Ala Lys Asn Ser Ser Cys Leu Pro Asn Pro Cys Val Asn
            725                 730                 735

Gly Gly Thr Cys Val Gly Ser Gly Ala Ser Phe Ser Cys Ile Cys Arg
        740                 745                 750

Asp Gly Trp Glu Gly Arg Thr Cys Thr His Asn Thr Asn Asp Cys Asn
    755                 760                 765

Pro Leu Pro Cys Tyr Asn Gly Gly Ile Cys Val Asp Gly Val Asn Trp
770                 775                 780

Phe Arg Cys Glu Cys Ala Pro Gly Phe Ala Gly Pro Asp Cys Arg Ile
785                 790                 795                 800

Asn Ile Asp Glu Cys Gln Ser Ser Pro Cys Ala Tyr Gly Ala Thr Cys
            805                 810                 815

Val Asp Glu Ile Asn Gly Tyr Arg Cys Ser Cys Pro Pro Gly Arg Ala
        820                 825                 830

Gly Pro Arg Cys Gln Glu Val Ile Gly Phe Gly Arg Ser Cys Trp Ser
    835                 840                 845

Arg Gly Thr Pro Phe Pro His Gly Ser Ser Trp Val Glu Asp Cys Asn
850                 855                 860

Ser Cys Arg Cys Leu Asp Gly Arg Arg Asp Cys Ser Lys Val Trp Cys
865                 870                 875                 880
```

```
Gly Trp Lys Pro Cys Leu Leu Ala Gly Gln Pro Glu Ala Leu Ser Ala
                885                 890                 895
Gln Cys Pro Leu Gly Gln Arg Cys Leu Glu Lys Ala Pro Gly Gln Cys
            900                 905                 910
Leu Arg Pro Pro Cys Glu Ala Trp Gly Glu Cys Gly Ala Glu Glu Pro
        915                 920                 925
Pro Ser Thr Pro Cys Leu Pro Arg Ser Gly His Leu Asp Asn Asn Cys
    930                 935                 940
Ala Arg Leu Thr Leu His Phe Asn Arg Asp His Val Pro Gln Gly Thr
945                 950                 955                 960
Thr Val Gly Ala Ile Cys Ser Gly Ile Arg Ser Leu Pro Ala Thr Arg
                965                 970                 975
Ala Val Ala Arg Asp Arg Leu Val Leu Leu Cys Asp Arg Ala Ser
            980                 985                 990
Ser Gly Ala Ser Ala Val Glu Val Ala Val Ser Phe Ser Pro Ala Arg
        995                 1000                1005
Asp Leu Pro Asp Ser Ser Leu Ile Gln Gly Ala Ala His Ala Ile Val
    1010                1015                1020
Ala Ala Ile Thr Gln Arg Gly Asn Ser Ser Leu Leu Leu Ala Val Thr
1025                1030                1035                1040
Glu Val Lys Val Glu Thr Val Val Thr Gly Gly Ser Ser Thr Gly
                1045                1050                1055

<210> SEQ ID NO 3
<211> LENGTH: 1212
<212> TYPE: PRT
<213> ORGANISM: Homo sapiens

<400> SEQUENCE: 3

Met Gly Tyr Phe Glu Leu Gln Leu Ser Ala Leu Arg Asn Val Asn Gly
 1               5                  10                  15
Glu Leu Leu Ser Gly Ala Cys Cys Asp Gly Asp Gly Arg Thr Thr Arg
                20                  25                  30
Ala Gly Gly Cys Gly His Asp Glu Cys Asp Thr Tyr Val Arg Val Cys
            35                  40                  45
Leu Lys Glu Tyr Gln Ala Lys Val Thr Pro Thr Gly Pro Cys Ser Tyr
    50                  55                  60
Gly His Gly Ala Thr Pro Val Leu Gly Gly Asn Ser Phe Tyr Leu Pro
65                  70                  75                  80
Pro Ala Gly Ala Ala Gly Asp Arg Ala Arg Ala Arg Ala Arg Ala Gly
                85                  90                  95
Gly Asp Gln Asp Pro Gly Leu Val Val Ile Pro Phe Gln Phe Ala Trp
            100                 105                 110
Pro Arg Ser Phe Thr Leu Ile Val Glu Ala Trp Asp Trp Asp Asn Asp
    115                 120                 125
Thr Thr Pro Asn Glu Glu Leu Leu Ile Glu Arg Val Ser His Ala Gly
130                 135                 140
Met Ile Asn Pro Glu Asp Arg Trp Lys Ser Leu His Phe Ser Gly His
145                 150                 155                 160
Val Ala His Leu Glu Leu Gln Ile Arg Val Arg Cys Asp Glu Asn Tyr
                165                 170                 175
Tyr Ser Ala Thr Cys Asn Lys Phe Cys Arg Pro Arg Asn Asp Phe Phe
            180                 185                 190
Gly His Tyr Thr Cys Asp Gln Tyr Gly Asn Lys Ala Cys Met Asp Gly
    195                 200                 205
```

-continued

```
Trp Met Gly Lys Glu Cys Lys Glu Ala Val Cys Lys Gln Gly Cys Asn
    210                 215                 220
Leu Leu His Gly Gly Cys Thr Val Pro Gly Glu Cys Arg Cys Ser Tyr
225                 230                 235                 240
Gly Trp Gln Gly Arg Phe Cys Asp Glu Cys Val Pro Tyr Pro Gly Cys
                    245                 250                 255
Val His Gly Ser Cys Val Glu Pro Trp Gln Cys Asn Cys Glu Thr Asn
                260                 265                 270
Trp Gly Gly Leu Leu Cys Asp Lys Asp Leu Asn Tyr Cys Gly Ser His
            275                 280                 285
His Pro Cys Thr Asn Gly Gly Thr Cys Ile Asn Ala Glu Pro Asp Gln
        290                 295                 300
Tyr Arg Cys Thr Cys Pro Asp Gly Tyr Ser Gly Arg Asn Cys Glu Lys
305                 310                 315                 320
Ala Glu His Ala Cys Thr Ser Asn Pro Cys Ala Asn Gly Gly Ser Cys
                    325                 330                 335
His Glu Val Pro Ser Gly Phe Glu Cys His Cys Pro Ser Gly Trp Ser
                340                 345                 350
Gly Pro Thr Cys Ala Leu Asp Ile Asp Glu Cys Ala Ser Asn Pro Cys
            355                 360                 365
Ala Ala Gly Gly Thr Cys Val Asp Gln Val Asp Gly Phe Glu Cys Ile
        370                 375                 380
Cys Pro Glu Gln Trp Val Gly Ala Thr Cys Gln Leu Asp Ala Asn Glu
385                 390                 395                 400
Cys Glu Gly Lys Pro Cys Leu Asn Ala Phe Ser Cys Lys Asn Leu Ile
                    405                 410                 415
Gly Gly Tyr Tyr Cys Asp Cys Ile Pro Gly Trp Lys Gly Ile Asn Cys
                420                 425                 430
His Ile Asn Val Asn Asp Cys Arg Gly Gln Cys Gln His Gly Gly Thr
            435                 440                 445
Cys Lys Asp Leu Val Asn Gly Tyr Gln Cys Val Cys Pro Arg Gly Phe
        450                 455                 460
Gly Gly Arg His Cys Glu Leu Glu Arg Asp Lys Cys Ala Ser Ser Pro
465                 470                 475                 480
Cys His Ser Gly Gly Leu Cys Glu Asp Leu Ala Asp Gly Phe His Cys
                    485                 490                 495
His Cys Pro Gln Gly Phe Ser Gly Pro Leu Cys Glu Val Asp Val Asp
                500                 505                 510
Leu Cys Glu Pro Ser Pro Cys Arg Asn Gly Ala Arg Cys Tyr Asn Leu
            515                 520                 525
Glu Gly Asp Tyr Tyr Cys Ala Cys Pro Asp Asp Phe Gly Gly Lys Asn
        530                 535                 540
Cys Ser Val Pro Arg Glu Pro Cys Pro Gly Gly Ala Cys Arg Val Ile
545                 550                 555                 560
Asp Gly Cys Gly Ser Asp Ala Gly Pro Gly Met Pro Gly Thr Ala Ala
                    565                 570                 575
Ser Gly Val Cys Gly Pro His Gly Arg Cys Val Ser Gln Pro Gly Gly
                580                 585                 590
Asn Phe Ser Cys Ile Cys Asp Ser Gly Phe Thr Gly Thr Tyr Cys His
            595                 600                 605
Glu Asn Ile Asp Asp Cys Leu Gly Gln Pro Cys Arg Asn Gly Gly Thr
        610                 615                 620
```

-continued

```
Cys Ile Asp Glu Val Asp Ala Phe Arg Cys Phe Cys Pro Ser Gly Trp
625                 630                 635                 640

Glu Gly Glu Leu Cys Asp Thr Asn Pro Asn Asp Cys Leu Pro Asp Pro
            645                 650                 655

Cys His Ser Arg Gly Arg Cys Tyr Asp Leu Val Asn Asp Phe Tyr Cys
        660                 665                 670

Ala Cys Asp Asp Gly Trp Lys Gly Lys Thr Cys His Ser Arg Glu Phe
    675                 680                 685

Gln Cys Asp Ala Tyr Thr Cys Ser Asn Gly Gly Thr Cys Tyr Asp Ser
690                 695                 700

Gly Asp Thr Phe Arg Cys Ala Cys Pro Pro Gly Trp Lys Gly Ser Thr
705                 710                 715                 720

Cys Ala Val Ala Lys Asn Ser Ser Cys Leu Pro Asn Pro Cys Val Asn
                725                 730                 735

Gly Gly Thr Cys Val Gly Ser Gly Ala Ser Phe Ser Cys Ile Cys Arg
            740                 745                 750

Asp Gly Trp Glu Gly Arg Thr Cys Thr His Asn Thr Asn Asp Cys Asn
        755                 760                 765

Pro Leu Pro Cys Tyr Asn Gly Gly Ile Cys Val Asp Gly Val Asn Trp
    770                 775                 780

Phe Arg Cys Glu Cys Ala Pro Gly Phe Ala Gly Pro Asp Cys Arg Ile
785                 790                 795                 800

Asn Ile Asp Glu Cys Gln Ser Ser Pro Cys Ala Tyr Gly Ala Thr Cys
                805                 810                 815

Val Asp Glu Ile Asn Gly Tyr Arg Cys Ser Cys Pro Pro Gly Arg Ala
            820                 825                 830

Gly Pro Arg Cys Gln Glu Val Ile Gly Phe Gly Arg Ser Cys Trp Ser
        835                 840                 845

Arg Gly Thr Pro Phe Pro His Gly Ser Ser Trp Val Glu Asp Cys Asn
    850                 855                 860

Ser Cys Arg Cys Leu Asp Gly Arg Arg Asp Cys Ser Lys Val Trp Cys
865                 870                 875                 880

Gly Trp Lys Pro Cys Leu Leu Ala Gly Gln Pro Glu Ala Leu Ser Ala
                885                 890                 895

Gln Cys Pro Leu Gly Gln Arg Cys Leu Glu Lys Ala Pro Gly Gln Cys
            900                 905                 910

Leu Arg Pro Pro Cys Glu Ala Trp Gly Glu Cys Gly Ala Glu Glu Pro
        915                 920                 925

Pro Ser Thr Pro Cys Leu Pro Arg Ser Gly His Leu Asp Asn Asn Cys
    930                 935                 940

Ala Arg Leu Thr Leu His Phe Asn Arg Asp His Val Pro Gln Gly Thr
945                 950                 955                 960

Thr Val Gly Ala Ile Cys Ser Gly Ile Arg Ser Leu Pro Ala Thr Arg
                965                 970                 975

Ala Val Ala Arg Asp Arg Leu Leu Val Leu Leu Cys Asp Arg Ala Ser
            980                 985                 990

Ser Gly Ala Ser Ala Val Glu Val Ala Val Ser Phe Ser Pro Ala Arg
        995                 1000                1005

Asp Leu Pro Asp Ser Ser Leu Ile Gln Gly Ala Ala His Ala Ile Val
    1010                1015                1020

Ala Ala Ile Thr Gln Arg Gly Asn Ser Ser Leu Leu Leu Ala Val Thr
1025                1030                1035                1040
```

-continued

```
Glu Val Lys Val Glu Thr Val Val Thr Gly Gly Ser Ser Thr Gly Leu
            1045                1050                1055
Leu Val Pro Val Leu Cys Gly Ala Phe Ser Val Leu Trp Leu Ala Cys
        1060                1065                1070
Val Val Leu Cys Val Trp Trp Thr Arg Lys Arg Arg Lys Glu Arg Glu
    1075                1080                1085
Arg Ser Arg Leu Pro Arg Glu Glu Ser Ala Asn Asn Gln Trp Ala Pro
    1090                1095                1100
Leu Asn Pro Ile Arg Asn Pro Ile Glu Arg Pro Gly Gly His Lys Asp
1105                1110                1115                1120
Val Leu Tyr Gln Cys Lys Asn Phe Thr Pro Pro Arg Arg Ala Asp
        1125                1130                1135
Glu Ala Leu Pro Gly Pro Ala Gly His Ala Ala Val Arg Glu Asp Glu
        1140                1145                1150
Glu Asp Glu Asp Leu Gly Arg Gly Glu Glu Asp Ser Leu Glu Ala Glu
    1155                1160                1165
Lys Phe Leu Ser His Lys Phe Thr Lys Asp Pro Gly Arg Ser Pro Gly
    1170                1175                1180
Arg Pro Ala His Trp Ala Ser Gly Pro Lys Val Asp Asn Arg Ala Val
1185                1190                1195                1200
Arg Ser Ile Asn Glu Ala Arg Tyr Ala Gly Lys Glu
        1205                1210
```

<210> SEQ ID NO 4
<211> LENGTH: 3955
<212> TYPE: DNA
<213> ORGANISM: Homo sapiens
<220> FEATURE:
<221> NAME/KEY: CDS
<222> LOCATION: (12)..(3725)
<221> NAME/KEY: sig_peptide
<222> LOCATION: (12)..(89)
<221> NAME/KEY: mat_peptide
<222> LOCATION: (90)..(3725)

<400> SEQUENCE: 4

```
tcgcgggggc a atg cgg gcg cag ggc cgg ggg cgc ctt ccc cgg cgg ctg        50
           Met Arg Ala Gln Gly Arg Gly Arg Leu Pro Arg Leu
             -25            -20            -15 ctg ctg ctg ctg gcg ctc tgg gtg cag gcg gcg cgg ccc atg ggc tat        98
Leu Leu Leu Leu Ala Leu Trp Val Gln Ala Ala Arg Pro Met Gly Tyr
    -10             -5             -1  1 ttc gag ctg cag ctg agc gcg ctg cgg aac gtg aac ggg gag ctg ctg       146
Phe Glu Leu Gln Leu Ser Ala Leu Arg Asn Val Asn Gly Glu Leu Leu
      5              10             15 agc ggc gcc tgc tgt gac ggc gac ggc cgg aca acg cgc gcg ggg ggc       194
Ser Gly Ala Cys Cys Asp Gly Asp Gly Arg Thr Thr Arg Ala Gly Gly
 20             25             30             35 tgc ggc cac gac gag tgc gac acg tac gtg cgc gtg tgc ctt aag gag       242
Cys Gly His Asp Glu Cys Asp Thr Tyr Val Arg Val Cys Leu Lys Glu
        40             45             50 tac cag gcc aag gtg acg ccc acg ggg ccc tgc agc tac ggc cac ggc       290
Tyr Gln Ala Lys Val Thr Pro Thr Gly Pro Cys Ser Tyr Gly His Gly
    55             60             65 gcc acg ccc gtg ctg ggc ggc aac tcc ttc tac ctg ccg ccg gcg ggc       338
Ala Thr Pro Val Leu Gly Gly Asn Ser Phe Tyr Leu Pro Pro Ala Gly
 70             75             80 gct gcg ggg gac cga gcg cgg gcg cgg gcc cgg gcc ggc ggc gac cag       386
Ala Ala Gly Asp Arg Ala Arg Ala Arg Ala Arg Ala Gly Gly Asp Gln
    85             90             95
```

```
gac ccg ggc ctc gtc gtc atc ccc ttc cag ttc gcc tgg ccg cgc tcc    434
Asp Pro Gly Leu Val Val Ile Pro Phe Gln Phe Ala Trp Pro Arg Ser
100             105                 110                 115 ttt acc ctc atc gtg gag gcc tgg gac tgg gac aac gat acc acc ccg    482
Phe Thr Leu Ile Val Glu Ala Trp Asp Trp Asp Asn Asp Thr Thr Pro
            120                 125                 130 aat gag gag ctg ctg atc gag cga gtg tcg cat gcc ggc atg atc aac    530
Asn Glu Glu Leu Leu Ile Glu Arg Val Ser His Ala Gly Met Ile Asn
                135                 140                 145 ccg gag gac cgc tgg aag agc ctg cac ttc agc ggc cac gtg gcg cac    578
Pro Glu Asp Arg Trp Lys Ser Leu His Phe Ser Gly His Val Ala His
        150                 155                 160 ctg gag ctg cag atc cgc gtg cgc tgc gac gag aac tac tac agc gcc    626
Leu Glu Leu Gln Ile Arg Val Arg Cys Asp Glu Asn Tyr Tyr Ser Ala
165                 170                 175 act tgc aac aag ttc tgc cgg ccc cgc aac gac ttt ttc ggc cac tac    674
Thr Cys Asn Lys Phe Cys Arg Pro Arg Asn Asp Phe Phe Gly His Tyr
180                 185                 190                 195 acc tgc gac cag tac ggc aac aag gcc tgc atg gac ggc tgg atg ggc    722
Thr Cys Asp Gln Tyr Gly Asn Lys Ala Cys Met Asp Gly Trp Met Gly
            200                 205                 210 aag gag tgc aag gaa gct gtg tgt aaa caa ggg tgt aat ttg ctc cac    770
Lys Glu Cys Lys Glu Ala Val Cys Lys Gln Gly Cys Asn Leu Leu His
                215                 220                 225 ggg gga tgc acc gtg cct ggg gag tgc agg tgc agc tac ggc tgg caa    818
Gly Gly Cys Thr Val Pro Gly Glu Cys Arg Cys Ser Tyr Gly Trp Gln
        230                 235                 240 ggg agg ttc tgc gat gag tgt gtc ccc tac ccc ggc tgc gtg cat ggc    866
Gly Arg Phe Cys Asp Glu Cys Val Pro Tyr Pro Gly Cys Val His Gly
245                 250                 255 agt tgt gtg gag ccc tgg cag tgc aac tgt gag acc aac tgg ggc ggc    914
Ser Cys Val Glu Pro Trp Gln Cys Asn Cys Glu Thr Asn Trp Gly Gly
260                 265                 270                 275 ctg ctc tgt gac aaa gac ctg aac tac tgt ggc agc cac cac ccc tgc    962
Leu Leu Cys Asp Lys Asp Leu Asn Tyr Cys Gly Ser His His Pro Cys
            280                 285                 290 acc aac gga ggc acg tgc atg aac gcc gag cct gac cag tac cgc tgc    1010
Thr Asn Gly Gly Thr Cys Met Asn Ala Glu Pro Asp Gln Tyr Arg Cys
                295                 300                 305 acc tgc cct gac ggc tac tcg ggc agg aac tgt gag aag gct gag cac    1058
Thr Cys Pro Asp Gly Tyr Ser Gly Arg Asn Cys Glu Lys Ala Glu His
        310                 315                 320 gcc tgc acc tcc aac ccg tgt gcc aac ggg ggc tct tgc cat gag gtg    1106
Ala Cys Thr Ser Asn Pro Cys Ala Asn Gly Gly Ser Cys His Glu Val
325                 330                 335 ccg tcc ggc ttc gaa tgc cac tgc cca tcg ggc tgg agc ggg ccc acc    1154
Pro Ser Gly Phe Glu Cys His Cys Pro Ser Gly Trp Ser Gly Pro Thr
340                 345                 350                 355 tgt gcc ctt gac atc gat gag tgt gct tcg aac ccg tgt gcg gcc ggt    1202
Cys Ala Leu Asp Ile Asp Glu Cys Ala Ser Asn Pro Cys Ala Ala Gly
            360                 365                 370 ggc acc tgt gtg gac cag gtg gac ggc ttt gag tgc atc tgc ccc gag    1250
Gly Thr Cys Val Asp Gln Val Asp Gly Phe Glu Cys Ile Cys Pro Glu
                375                 380                 385 cag tgg gtg ggg gcc acc tgc cag ctg gac gcc aat gag tgt gaa ggg    1298
Gln Trp Val Gly Ala Thr Cys Gln Leu Asp Ala Asn Glu Cys Glu Gly
        390                 395                 400 aag cca tgc ctt aac gct ttt tct tgc aaa aac ctg att ggc ggc tat    1346
Lys Pro Cys Leu Asn Ala Phe Ser Cys Lys Asn Leu Ile Gly Gly Tyr
405                 410                 415
```

```
tac tgt gat tgc atc ccg ggc tgg aag ggc atc aac tgc cat atc aac    1394
Tyr Cys Asp Cys Ile Pro Gly Trp Lys Gly Ile Asn Cys His Ile Asn
420                 425                 430                 435 gtc aac gac tgt cgc ggg cag tgt cag cat ggg ggc acc tgc aag gac    1442
Val Asn Asp Cys Arg Gly Gln Cys Gln His Gly Gly Thr Cys Lys Asp
            440                 445                 450 ctg gtg aac ggg tac cag tgt gtg tgc cca cgg ggc ttc gga ggc cgg    1490
Leu Val Asn Gly Tyr Gln Cys Val Cys Pro Arg Gly Phe Gly Gly Arg
    455                 460                 465 cat tgc gag ctg gaa cga gac aag tgt gcc agc agc ccc tgc cac agc    1538
His Cys Glu Leu Glu Arg Asp Lys Cys Ala Ser Ser Pro Cys His Ser
470                 475                 480 ggc ggc ctc tgc gag gac ctg gcc gac ggc ttc cac tgc cac tgc ccc    1586
Gly Gly Leu Cys Glu Asp Leu Ala Asp Gly Phe His Cys His Cys Pro
            485                 490                 495 cag ggc ttc tcc ggg cct ctc tgt gag gtg gat gtc gac ctt tgt gag    1634
Gln Gly Phe Ser Gly Pro Leu Cys Glu Val Asp Val Asp Leu Cys Glu
500                 505                 510                 515 cca agc ccc tgc cgg aac ggc gct cgc tgc tat aac ctg gag ggt gac    1682
Pro Ser Pro Cys Arg Asn Gly Ala Arg Cys Tyr Asn Leu Glu Gly Asp
        520                 525                 530 tat tac tgc gcc tgc cct gat gac ttt ggt ggc aag aac tgc tcc gtg    1730
Tyr Tyr Cys Ala Cys Pro Asp Asp Phe Gly Gly Lys Asn Cys Ser Val
            535                 540                 545 ccc cgc gag ccg tgc cct ggg ggc gcc tgc aga gtg atc gat ggc tgc    1778
Pro Arg Glu Pro Cys Pro Gly Gly Ala Cys Arg Val Ile Asp Gly Cys
550                 555                 560 ggg tca gac gcg ggg cct ggg atg cct ggc aca gca gcc tcc ggc gtg    1826
Gly Ser Asp Ala Gly Pro Gly Met Pro Gly Thr Ala Ala Ser Gly Val
    565                 570                 575 tgt ggc ccc cat gga cgc tgc gtc agc cag cca ggg ggc aac ttt tcc    1874
Cys Gly Pro His Gly Arg Cys Val Ser Gln Pro Gly Gly Asn Phe Ser
580                 585                 590                 595 tgc atc tgt gac agt ggc ttt act ggc acc tac tgc cat gag aac att    1922
Cys Ile Cys Asp Ser Gly Phe Thr Gly Thr Tyr Cys His Glu Asn Ile
            600                 605                 610 gac gac tgc ctg ggc cag ccc tgc cgc aat ggg ggc aca tgc atc gat    1970
Asp Asp Cys Leu Gly Gln Pro Cys Arg Asn Gly Gly Thr Cys Ile Asp
        615                 620                 625 gag gtg gac gcc ttc cgc tgc ttc tgc ccc agc ggc tgg gag ggc gag    2018
Glu Val Asp Ala Phe Arg Cys Phe Cys Pro Ser Gly Trp Glu Gly Glu
            630                 635                 640 ctc tgc gac acc aat ccc aac gac tgc ctt ccc gat ccc tgc cac agc    2066
Leu Cys Asp Thr Asn Pro Asn Asp Cys Leu Pro Asp Pro Cys His Ser
645                 650                 655 cgc ggc cgc tgc tac gac ctg gtc aat gac ttc tac tgt gcg tgc gac    2114
Arg Gly Arg Cys Tyr Asp Leu Val Asn Asp Phe Tyr Cys Ala Cys Asp
660                 665                 670                 675 gac ggc tgg aag ggc aag acc tgc cac tca cgc gag ttc cag tgc gat    2162
Asp Gly Trp Lys Gly Lys Thr Cys His Ser Arg Glu Phe Gln Cys Asp
            680                 685                 690 gcc tac acc tgc agc aac ggt ggc acc tgc tac gac agc ggc gac acc    2210
Ala Tyr Thr Cys Ser Asn Gly Gly Thr Cys Tyr Asp Ser Gly Asp Thr
        695                 700                 705 ttc cgc tgc gcc tgg ccc ccc ggc tgg aag ggc agc acc tgc gcc gtc    2258
Phe Arg Cys Ala Trp Pro Pro Gly Trp Lys Gly Ser Thr Cys Ala Val
            710                 715                 720 gcc aag aac agc agc tgc ctg ccc aac ccc tgt gtg aat ggt ggc acc    2306
Ala Lys Asn Ser Ser Cys Leu Pro Asn Pro Cys Val Asn Gly Gly Thr
725                 730                 735
```

```
                                                       -continued
tgc gtg ggc agc ggg gcc tcc ttc tcc tgc atc tgc cgg gac ggc tgg    2354
Cys Val Gly Ser Gly Ala Ser Phe Ser Cys Ile Cys Arg Asp Gly Trp
740                 745                 750                 755 gag ggt cgt act tgc act cac aat acc aac gac tgc aac cct ctg cct    2402
Glu Gly Arg Thr Cys Thr His Asn Thr Asn Asp Cys Asn Pro Leu Pro
            760                 765                 770 tgc tac aat ggt ggc atc tgt gtt gac ggc gtc aac tgg ttc cgc tgc    2450
Cys Tyr Asn Gly Gly Ile Cys Val Asp Gly Val Asn Trp Phe Arg Cys
        775                 780                 785 gag tgt gca cct ggc ttc gcg ggg cct gac tgc cgc atc aac atc gac    2498
Glu Cys Ala Pro Gly Phe Ala Gly Pro Asp Cys Arg Ile Asn Ile Asp
    790                 795                 800 gag tgc cag tcc tcg ccc tgt gcc tac ggg gcc acg tgt gtg gat gag    2546
Glu Cys Gln Ser Ser Pro Cys Ala Tyr Gly Ala Thr Cys Val Asp Glu
805                 810                 815 atc aac ggg tat cgc tgt agc tgc cca ccc ggc cga gcc ggc ccc cgg    2594
Ile Asn Gly Tyr Arg Cys Ser Cys Pro Pro Gly Arg Ala Gly Pro Arg
820                 825                 830                 835 tgc cag gaa gtg atc ggg ttc ggg aga tcc tgc tgg tcc cgg ggc act    2642
Cys Gln Glu Val Ile Gly Phe Gly Arg Ser Cys Trp Ser Arg Gly Thr
            840                 845                 850 ccg ttc cca cac gga agc tcc tgg gtg gaa gac tgc aac agc tgc cgc    2690
Pro Phe Pro His Gly Ser Ser Trp Val Glu Asp Cys Asn Ser Cys Arg
        855                 860                 865 tgc ctg gat ggc cgc cgt gac tgc agc aag gtg tgg tgc gga tgg aag    2738
Cys Leu Asp Gly Arg Arg Asp Cys Ser Lys Val Trp Cys Gly Trp Lys
    870                 875                 880 cct tgt ctg ctg gcc ggc cag ccc gag gcc ctg agc gcc cag tgc cca    2786
Pro Cys Leu Leu Ala Gly Gln Pro Glu Ala Leu Ser Ala Gln Cys Pro
885                 890                 895 ctg ggg caa agg tgc ctg gag aag gcc cca ggc cag tgt ctc cga cca    2834
Leu Gly Gln Arg Cys Leu Glu Lys Ala Pro Gly Gln Cys Leu Arg Pro
900                 905                 910                 915 ccc tgt gag gcc tgg ggg gag tgc ggc gca gaa gag cca ccg agc acc    2882
Pro Cys Glu Ala Trp Gly Glu Cys Gly Ala Glu Glu Pro Pro Ser Thr
            920                 925                 930 ccc tgc ctg cca cgc tcc ggc cac ctg gac aat aac tgt gcc cgc ctc    2930
Pro Cys Leu Pro Arg Ser Gly His Leu Asp Asn Asn Cys Ala Arg Leu
        935                 940                 945 acc ttg cat ttc aac cgt gac cac gtg ccc cag ggc acc acg gtg ggc    2978
Thr Leu His Phe Asn Arg Asp His Val Pro Gln Gly Thr Thr Val Gly
    950                 955                 960 gcc att tgc tcc ggg atc cgc tcc ctg cca gcc aca agg gct gtg gca    3026
Ala Ile Cys Ser Gly Ile Arg Ser Leu Pro Ala Thr Arg Ala Val Ala
965                 970                 975 cgg gac cgc ctg ctg gtg ttg ctt tgc gac cgg gcg tcc tcg ggg gcc    3074
Arg Asp Arg Leu Leu Val Leu Leu Cys Asp Arg Ala Ser Ser Gly Ala
980                 985                 990                 995 agt gcc gtg gag gtg gcc gtg tcc ttc agc cct gcc agg gac ctg cct    3122
Ser Ala Val Glu Val Ala Val Ser Phe Ser Pro Ala Arg Asp Leu Pro
            1000                1005                1010 gac agc agc ctg atc cag ggc gcg gcc cac gcc atc gtg gcc gcc atc    3170
Asp Ser Ser Leu Ile Gln Gly Ala Ala His Ala Ile Val Ala Ala Ile
        1015                1020                1025 acc cag cgg ggg aac agc tca ctg ctc ctg gct gtc acc gag gtc aag    3218
Thr Gln Arg Gly Asn Ser Ser Leu Leu Leu Ala Val Thr Glu Val Lys
    1030                1035                1040 gtg gag acg gtt gtt acg ggc ggc tct tcc aca ggt ctg ctg gtg cct    3266
Val Glu Thr Val Val Thr Gly Gly Ser Ser Thr Gly Leu Leu Val Pro
1045                1050                1055
```

-continued

| | |
|---|---|
| gtg ctg tgt ggt gcc ttc agc gtg ctg tgg ctg gcg tgc gtg gtc ctg<br>Val Leu Cys Gly Ala Phe Ser Val Leu Trp Leu Ala Cys Val Val Leu<br>1060                    1065                    1070                    1075 | 3314 |
| tgc gtg tgg tgg aca cgc aag cgc agg aaa gag cgg gag agg agc cgg<br>Cys Val Trp Trp Thr Arg Lys Arg Arg Lys Glu Arg Glu Arg Ser Arg<br>                1080                    1085                    1090 | 3362 |
| ctg ccg cgg gag gag agc gcc aac aac cag tgg gcc ccg ctc aac ccc<br>Leu Pro Arg Glu Glu Ser Ala Asn Asn Gln Trp Ala Pro Leu Asn Pro<br>1095                    1100                    1105 | 3410 |
| atc cgc aac ccc atc gag cgg ccg ggg ggc cac aag gac gtg ctc tac<br>Ile Arg Asn Pro Ile Glu Arg Pro Gly Gly His Lys Asp Val Leu Tyr<br>                1110                    1115                    1120 | 3458 |
| cag tgc aag aac ttc acg ccg ccg ccg cgc agg gcg gac gag gcg ctg<br>Gln Cys Lys Asn Phe Thr Pro Pro Pro Arg Arg Ala Asp Glu Ala Leu<br>1125                    1130                    1135 | 3506 |
| ccc ggg ccg gcc ggc cac gcg gcc gtc agg gag gat gag gag gac gag<br>Pro Gly Pro Ala Gly His Ala Ala Val Arg Glu Asp Glu Glu Asp Glu<br>1140                    1145                    1150                    1155 | 3554 |
| gat ctg ggc cgc ggt gag gag gac tcc ctg gag gcg gag aag ttc ctc<br>Asp Leu Gly Arg Gly Glu Glu Asp Ser Leu Glu Ala Glu Lys Phe Leu<br>                1160                    1165                    1170 | 3602 |
| tca cac aaa ttc acc aaa gat cct ggc cgc tcg ccg ggg agg ccg gcc<br>Ser His Lys Phe Thr Lys Asp Pro Gly Arg Ser Pro Gly Arg Pro Ala<br>1175                    1180                    1185 | 3650 |
| cac tgg gcc tca ggc ccc aaa gtg gac aac cgc gcg gtc agg agc atc<br>His Trp Ala Ser Gly Pro Lys Val Asp Asn Arg Ala Val Arg Ser Ile<br>1190                    1195                    1200 | 3698 |
| aat gag gcc cgc tac gcc ggc aag gag tagggcggc tgccagctgg<br>Asn Glu Ala Arg Tyr Ala Gly Lys Glu<br>1205                    1210 | 3745 |
| gccgggaccc agggccctcg gtgggagcca tgccgtctgc cggacccgga ggccgaggcc | 3805 |
| atgtgcatag tttctttatt ttgtgtaaaa aaccaccaa aaacaaaaac caaatgttta | 3865 |
| ttttctacgt ttctttaacc ttgtataaat tattcagtaa ctgtcaggct gaaaacaatg | 3925 |
| gagtattctc ggaaaaaaaa aaaaaaaaaa | 3955 |

<210> SEQ ID NO 5
<211> LENGTH: 1238
<212> TYPE: PRT
<213> ORGANISM: Homo sapiens

<400> SEQUENCE: 5

Met Arg Ala Gln Gly Arg Gly Arg Leu Pro Arg Leu Leu Leu Leu
    -25                    -20                    -15

Leu Ala Leu Trp Val Gln Ala Ala Arg Pro Met Gly Tyr Phe Glu Leu
-10                    -5                  -1   1                 5

Gln Leu Ser Ala Leu Arg Asn Val Asn Gly Glu Leu Leu Ser Gly Ala
          10                    15                    20

Cys Cys Asp Gly Asp Gly Arg Thr Thr Arg Ala Gly Gly Cys Gly His
            25                    30                    35

Asp Glu Cys Asp Thr Tyr Val Arg Val Cys Leu Lys Glu Tyr Gln Ala
    40                    45                    50

Lys Val Thr Pro Thr Gly Pro Cys Ser Tyr Gly His Gly Ala Thr Pro
55                    60                    65                    70

Val Leu Gly Gly Asn Ser Phe Tyr Leu Pro Pro Ala Gly Ala Ala Gly
            75                    80                    85

Asp Arg Ala Arg Ala Arg Ala Arg Ala Gly Gly Asp Gln Asp Pro Gly
    90                    95                    100

-continued

```
Leu Val Val Ile Pro Phe Gln Phe Ala Trp Pro Arg Ser Phe Thr Leu
        105                 110                 115
Ile Val Glu Ala Trp Asp Trp Asp Asn Asp Thr Thr Pro Asn Glu Glu
    120                 125                 130
Leu Leu Ile Glu Arg Val Ser His Ala Gly Met Ile Asn Pro Glu Asp
135                 140                 145                 150
Arg Trp Lys Ser Leu His Phe Ser Gly His Val Ala His Leu Glu Leu
                155                 160                 165
Gln Ile Arg Val Arg Cys Asp Glu Asn Tyr Tyr Ser Ala Thr Cys Asn
            170                 175                 180
Lys Phe Cys Arg Pro Arg Asn Asp Phe Phe Gly His Tyr Thr Cys Asp
        185                 190                 195
Gln Tyr Gly Asn Lys Ala Cys Met Asp Gly Trp Met Gly Lys Glu Cys
    200                 205                 210
Lys Glu Ala Val Cys Lys Gln Gly Cys Asn Leu Leu His Gly Gly Cys
215                 220                 225                 230
Thr Val Pro Gly Glu Cys Arg Cys Ser Tyr Gly Trp Gln Gly Arg Phe
                235                 240                 245
Cys Asp Glu Cys Val Pro Tyr Pro Gly Cys Val His Gly Ser Cys Val
            250                 255                 260
Glu Pro Trp Gln Cys Asn Cys Glu Thr Asn Trp Gly Gly Leu Leu Cys
        265                 270                 275
Asp Lys Asp Leu Asn Tyr Cys Gly Ser His His Pro Cys Thr Asn Gly
    280                 285                 290
Gly Thr Cys Met Asn Ala Glu Pro Asp Gln Tyr Arg Cys Thr Cys Pro
295                 300                 305                 310
Asp Gly Tyr Ser Gly Arg Asn Cys Glu Lys Ala Glu His Ala Cys Thr
                315                 320                 325
Ser Asn Pro Cys Ala Asn Gly Gly Ser Cys His Glu Val Pro Ser Gly
            330                 335                 340
Phe Glu Cys His Cys Pro Ser Gly Trp Ser Gly Pro Thr Cys Ala Leu
        345                 350                 355
Asp Ile Asp Glu Cys Ala Ser Asn Pro Cys Ala Ala Gly Gly Thr Cys
    360                 365                 370
Val Asp Gln Val Asp Gly Phe Glu Cys Ile Cys Pro Glu Gln Trp Val
375                 380                 385                 390
Gly Ala Thr Cys Gln Leu Asp Ala Asn Glu Cys Glu Gly Lys Pro Cys
                395                 400                 405
Leu Asn Ala Phe Ser Cys Lys Asn Leu Ile Gly Gly Tyr Tyr Cys Asp
            410                 415                 420
Cys Ile Pro Gly Trp Lys Gly Ile Asn Cys His Ile Asn Val Asn Asp
        425                 430                 435
Cys Arg Gly Gln Cys Gln His Gly Gly Thr Cys Lys Asp Leu Val Asn
    440                 445                 450
Gly Tyr Gln Cys Val Cys Pro Arg Gly Phe Gly Gly Arg His Cys Glu
455                 460                 465                 470
Leu Glu Arg Asp Lys Cys Ala Ser Ser Pro Cys His Ser Gly Gly Leu
                475                 480                 485
Cys Glu Asp Leu Ala Asp Gly Phe His Cys His Cys Pro Gln Gly Phe
            490                 495                 500
Ser Gly Pro Leu Cys Glu Val Asp Val Asp Leu Cys Glu Pro Ser Pro
        505                 510                 515
```

```
Cys Arg Asn Gly Ala Arg Cys Tyr Asn Leu Glu Gly Asp Tyr Tyr Cys
520                 525                 530

Ala Cys Pro Asp Asp Phe Gly Gly Lys Asn Cys Ser Val Pro Arg Glu
535                 540                 545                 550

Pro Cys Pro Gly Gly Ala Cys Arg Val Ile Asp Gly Cys Gly Ser Asp
            555                 560                 565

Ala Gly Pro Gly Met Pro Gly Thr Ala Ala Ser Gly Val Cys Gly Pro
            570                 575                 580

His Gly Arg Cys Val Ser Gln Pro Gly Gly Asn Phe Ser Cys Ile Cys
            585                 590                 595

Asp Ser Gly Phe Thr Gly Thr Tyr Cys His Glu Asn Ile Asp Asp Cys
600                 605                 610

Leu Gly Gln Pro Cys Arg Asn Gly Gly Thr Cys Ile Asp Glu Val Asp
615                 620                 625                 630

Ala Phe Arg Cys Phe Cys Pro Ser Gly Trp Glu Gly Glu Leu Cys Asp
            635                 640                 645

Thr Asn Pro Asn Asp Cys Leu Pro Asp Pro Cys His Ser Arg Gly Arg
            650                 655                 660

Cys Tyr Asp Leu Val Asn Asp Phe Tyr Cys Ala Cys Asp Asp Gly Trp
            665                 670                 675

Lys Gly Lys Thr Cys His Ser Arg Glu Phe Gln Cys Asp Ala Tyr Thr
            680                 685                 690

Cys Ser Asn Gly Gly Thr Cys Tyr Asp Ser Gly Asp Thr Phe Arg Cys
695                 700                 705                 710

Ala Trp Pro Pro Gly Trp Lys Gly Ser Thr Cys Ala Val Ala Lys Asn
            715                 720                 725

Ser Ser Cys Leu Pro Asn Pro Cys Val Asn Gly Thr Cys Val Gly
            730                 735                 740

Ser Gly Ala Ser Phe Ser Cys Ile Cys Arg Asp Gly Trp Glu Gly Arg
            745                 750                 755

Thr Cys Thr His Asn Thr Asn Asp Cys Asn Pro Leu Pro Cys Tyr Asn
            760                 765                 770

Gly Gly Ile Cys Val Asp Gly Val Asn Trp Phe Arg Cys Glu Cys Ala
775                 780                 785                 790

Pro Gly Phe Ala Gly Pro Asp Cys Arg Ile Asn Ile Asp Glu Cys Gln
            795                 800                 805

Ser Ser Pro Cys Ala Tyr Gly Ala Thr Cys Val Asp Glu Ile Asn Gly
            810                 815                 820

Tyr Arg Cys Ser Cys Pro Pro Gly Arg Ala Gly Pro Arg Cys Gln Glu
            825                 830                 835

Val Ile Gly Phe Gly Arg Ser Cys Trp Ser Arg Gly Thr Pro Phe Pro
840                 845                 850

His Gly Ser Ser Trp Val Glu Asp Cys Asn Ser Cys Arg Cys Leu Asp
855                 860                 865                 870

Gly Arg Arg Asp Cys Ser Lys Val Trp Cys Gly Trp Lys Pro Cys Leu
            875                 880                 885

Leu Ala Gly Gln Pro Glu Ala Leu Ser Ala Gln Cys Pro Leu Gly Gln
            890                 895                 900

Arg Cys Leu Glu Lys Ala Pro Gly Gln Cys Leu Arg Pro Cys Glu
            905                 910                 915

Ala Trp Gly Glu Cys Gly Ala Glu Glu Pro Pro Ser Thr Pro Cys Leu
920                 925                 930
```

-continued

Pro Arg Ser Gly His Leu Asp Asn Asn Cys Ala Arg Leu Thr Leu His
935                 940                 945                 950

Phe Asn Arg Asp His Val Pro Gln Gly Thr Thr Val Gly Ala Ile Cys
            955                 960                 965

Ser Gly Ile Arg Ser Leu Pro Ala Thr Arg Ala Val Ala Arg Asp Arg
        970                 975                 980

Leu Leu Val Leu Leu Cys Asp Arg Ala Ser Gly Ala Ser Ala Val
    985                 990                 995

Glu Val Ala Val Ser Phe Ser Pro Ala Arg Asp Leu Pro Asp Ser Ser
1000                1005                1010

Leu Ile Gln Gly Ala Ala His Ala Ile Val Ala Ala Ile Thr Gln Arg
1015                1020                1025                1030

Gly Asn Ser Ser Leu Leu Leu Ala Val Thr Glu Val Lys Val Glu Thr
                1035                1040                1045

Val Val Thr Gly Gly Ser Ser Thr Gly Leu Leu Val Pro Val Leu Cys
                1050                1055                1060

Gly Ala Phe Ser Val Leu Trp Leu Ala Cys Val Val Leu Cys Val Trp
        1065                1070                1075

Trp Thr Arg Lys Arg Arg Lys Glu Arg Glu Arg Ser Arg Leu Pro Arg
    1080                1085                1090

Glu Glu Ser Ala Asn Asn Gln Trp Ala Pro Leu Asn Pro Ile Arg Asn
1095                1100                1105                1110

Pro Ile Glu Arg Pro Gly Gly His Lys Asp Val Leu Tyr Gln Cys Lys
                1115                1120                1125

Asn Phe Thr Pro Pro Arg Arg Ala Asp Glu Ala Leu Pro Gly Pro
            1130                1135                1140

Ala Gly His Ala Ala Val Arg Glu Asp Glu Glu Asp Glu Asp Leu Gly
            1145                1150                1155

Arg Gly Glu Glu Asp Ser Leu Glu Ala Glu Lys Phe Leu Ser His Lys
1160                1165                1170

Phe Thr Lys Asp Pro Gly Arg Ser Pro Gly Arg Pro Ala His Trp Ala
1175                1180                1185                1190

Ser Gly Pro Lys Val Asp Asn Arg Ala Val Arg Ser Ile Asn Glu Ala
            1195                1200                1205

Arg Tyr Ala Gly Lys Glu
            1210

<210> SEQ ID NO 6
<211> LENGTH: 4208
<212> TYPE: DNA
<213> ORGANISM: Homo sapiens
<220> FEATURE:
<221> NAME/KEY: CDS
<222> LOCATION: (409)..(4062)
<221> NAME/KEY: sig_peptide
<222> LOCATION: (409)..(501)
<221> NAME/KEY: mat_peptide
<222> LOCATION: (502)..(4062)

<400> SEQUENCE: 6
ggccggcccg cgagctaggc tggtttttttt ttttctcccc tccctccccc cttttccat      60 gcagctgatc taaagggaa taaaggctg cgcataatca taataataaa agaaggggag     120
cgcgagagaa ggaaagaaag ccgggaggtg gaagaggagg gggagcgtct caaagaagcg     180
atcagaataa taaaggagg ccgggctctt tgccttctgg aacgggccgc tcttgaaagg     240
gcttttgaaa agtggtgttg ttttccagtc gtgcatgctc caatcggcgg agtatattag     300

-continued

```
agccgggacg cggcggccgc aggggcagcg gcgacggcag caccggcggc agcaccagcg        360
cgaacagcag cggcggcgtc ccgagtgccc gcggcgcgcg gcgcagcg atg cgt tcc        417
                                                     Met Arg Ser
                                                     -30 cca cgg acg cgc ggc cgg tcc ggg cgc ccc cta agc ctc ctg ctc gcc        465
Pro Arg Thr Arg Gly Arg Ser Gly Arg Pro Leu Ser Leu Leu Leu Ala
        -25             -20                 -15 ctg ctc tgt gcc ctg cga gcc aag gtg tgt ggg gcc tcg ggt cag ttc        513
Leu Leu Cys Ala Leu Arg Ala Lys Val Cys Gly Ala Ser Gly Gln Phe
    -10              -5                  -1  1 gag ttg gag atc ctg tcc atg cag aac gtg aac ggg gag ctg cag aac        561
Glu Leu Glu Ile Leu Ser Met Gln Asn Val Asn Gly Glu Leu Gln Asn
 5                  10                  15                  20 ggg aac tgc tgc ggc ggc gcc cgg aac ccg gga gac cgc aag tgc acc        609
Gly Asn Cys Cys Gly Gly Ala Arg Asn Pro Gly Asp Arg Lys Cys Thr
             25                  30                  35 cgc gac gag tct gac aca tac ttc aaa gtg tgc ctc aag gag tat cag        657
Arg Asp Glu Ser Asp Thr Tyr Phe Lys Val Cys Leu Lys Glu Tyr Gln
             40                  45                  50 tcc cgc gtc acg gcc ggg ggg ccc tgc agc ttc ggc tca ggg tcc acg        705
Ser Arg Val Thr Ala Gly Gly Pro Cys Ser Phe Gly Ser Gly Ser Thr
         55                  60                  65 cct gtc atc ggg ggc aac acc ttc aac ctc aag gcc agc cgc ggc aac        753
Pro Val Ile Gly Gly Asn Thr Phe Asn Leu Lys Ala Ser Arg Gly Asn
     70                  75                  80 gac cgc aac cgc atc gtg ctg cct ttc agt ttc gcc tgg ccg agg tcc        801
Asp Arg Asn Arg Ile Val Leu Pro Phe Ser Phe Ala Trp Pro Arg Ser
 85                  90                  95                 100 tat acg ttg ctt gtg gag gcg tgg gat tcc agt aat gac acc gtt caa        849
Tyr Thr Leu Leu Val Glu Ala Trp Asp Ser Ser Asn Asp Thr Val Gln
                 105                 110                 115 cct gac agt att att gaa aag gct tct cac tcg ggc atg atc aac ccc        897
Pro Asp Ser Ile Ile Glu Lys Ala Ser His Ser Gly Met Ile Asn Pro
             120                 125                 130 agc cgg cag tgg cag acg ctg aag cag aac acg ggc gtt gcc cac ttt        945
Ser Arg Gln Trp Gln Thr Leu Lys Gln Asn Thr Gly Val Ala His Phe
         135                 140                 145 gag tat cag atc cgc gtg acc tgt gat gac tac tat ggc ttt ggc           993
Glu Tyr Gln Ile Arg Val Thr Cys Asp Asp Tyr Tyr Tyr Gly Phe Gly
     150                 155                 160 tgc aat aag ttc tgc cgc ccc aga gat gac ttc ttt gga cac tat gcc       1041
Cys Asn Lys Phe Cys Arg Pro Arg Asp Asp Phe Phe Gly His Tyr Ala
165                 170                 175                 180 tgt gac cag aat ggc aac aaa act tgc atg gaa ggc tgg atg ggc ccc       1089
Cys Asp Gln Asn Gly Asn Lys Thr Cys Met Glu Gly Trp Met Gly Pro
                185                 190                 195 gaa tgt aac aga gct att tgc cga caa ggc tgc agt cct aag cat ggg       1137
Glu Cys Asn Arg Ala Ile Cys Arg Gln Gly Cys Ser Pro Lys His Gly
            200                 205                 210 tct tgc aaa ctc cca ggt gac tgc agg tgc cag tac ggc tgg caa ggc       1185
Ser Cys Lys Leu Pro Gly Asp Cys Arg Cys Gln Tyr Gly Trp Gln Gly
        215                 220                 225 ctg tac tgt gat aag tgc atc cca cac ccg gga tgc gtc cac ggc atc       1233
Leu Tyr Cys Asp Lys Cys Ile Pro His Pro Gly Cys Val His Gly Ile
    230                 235                 240 tgt aat gag ccc tgg cag tgc ctc tgt gag acc aac tgg ggc ggc cag       1281
Cys Asn Glu Pro Trp Gln Cys Leu Cys Glu Thr Asn Trp Gly Gly Gln
245                 250                 255                 260
```

```
ctc tgt gac aaa gat ctc aat tac tgt ggg act cat cag ccg tgt ctc    1329
Leu Cys Asp Lys Asp Leu Asn Tyr Cys Gly Thr His Gln Pro Cys Leu
            265                 270                 275 aac ggg gga act tgt agc aac aca ggc cct gac aaa tat cag tgt tcc    1377
Asn Gly Gly Thr Cys Ser Asn Thr Gly Pro Asp Lys Tyr Gln Cys Ser
        280                 285                 290 tgc cct gag ggg tat tca gga ccc aac tct gaa att gct gag cac gcc    1425
Cys Pro Glu Gly Tyr Ser Gly Pro Asn Ser Glu Ile Ala Glu His Ala
    295                 300                 305 tgc ctc tct gat ccc tgt cac aac aga ggc agc tgt aag gag acc tcc    1473
Cys Leu Ser Asp Pro Cys His Asn Arg Gly Ser Cys Lys Glu Thr Ser
310                 315                 320 ctg ggc ttt gag tgt gag tgt tcc cca ggc tgg acc ggc ccc aca tgc    1521
Leu Gly Phe Glu Cys Glu Cys Ser Pro Gly Trp Thr Gly Pro Thr Cys
325                 330                 335                 340 tct aca aac att gat gac tgt tct cct aat aac tgt tcc cac ggg ggc    1569
Ser Thr Asn Ile Asp Asp Cys Ser Pro Asn Asn Cys Ser His Gly Gly
                345                 350                 355 acc tgc cag gac ctg gtt aac gga ttt aag tgt gtg tgc ccc cca cag    1617
Thr Cys Gln Asp Leu Val Asn Gly Phe Lys Cys Val Cys Pro Pro Gln
            360                 365                 370 tgg act ggg aaa acg tgc cag tta gat gca aat gaa tgt gag gcc aaa    1665
Trp Thr Gly Lys Thr Cys Gln Leu Asp Ala Asn Glu Cys Glu Ala Lys
        375                 380                 385 cct tgt gta aac gcc aaa tcc tgt aag aat ctc att gcc agc tac tac    1713
Pro Cys Val Asn Ala Lys Ser Cys Lys Asn Leu Ile Ala Ser Tyr Tyr
    390                 395                 400 tgc gac tgt ctt ccc ggc tgg atg ggt cag aat tgt gac ata aat att    1761
Cys Asp Cys Leu Pro Gly Trp Met Gly Gln Asn Cys Asp Ile Asn Ile
405                 410                 415                 420 aat gac tgc ctt ggc cag tgt cag aat gac gcc tcc tgt cgg gat ttg    1809
Asn Asp Cys Leu Gly Gln Cys Gln Asn Asp Ala Ser Cys Arg Asp Leu
                425                 430                 435 gtt aat ggt tat cgc tgt atc tgt cca cct ggc tat gca ggc gat cac    1857
Val Asn Gly Tyr Arg Cys Ile Cys Pro Pro Gly Tyr Ala Gly Asp His
            440                 445                 450 tgt gag aga gac atc gat gaa tgt gcc agc aac ccc tgt ttg aat ggg    1905
Cys Glu Arg Asp Ile Asp Glu Cys Ala Ser Asn Pro Cys Leu Asn Gly
        455                 460                 465 ggt cac tgt cag aat gaa atc aac aga ttc cag tgt ctg tgt ccc act    1953
Gly His Cys Gln Asn Glu Ile Asn Arg Phe Gln Cys Leu Cys Pro Thr
    470                 475                 480 ggt ttc tct gga aac ctc tgt cag ctg gac atc gat tat tgt gag cct    2001
Gly Phe Ser Gly Asn Leu Cys Gln Leu Asp Ile Asp Tyr Cys Glu Pro
485                 490                 495                 500 aat ccc tgc cag aac ggt gcc cag tgc tac aac cgt gcc agt gac tat    2049
Asn Pro Cys Gln Asn Gly Ala Gln Cys Tyr Asn Arg Ala Ser Asp Tyr
                505                 510                 515 ttc tgc aag tgc ccc gag gac tat gag ggc aag aac tgc tca cac ctg    2097
Phe Cys Lys Cys Pro Glu Asp Tyr Glu Gly Lys Asn Cys Ser His Leu
            520                 525                 530 aaa gac cac tgc cgc acg acc ccc tgt gaa gtg att gac agc tgc aca    2145
Lys Asp His Cys Arg Thr Thr Pro Cys Glu Val Ile Asp Ser Cys Thr
        535                 540                 545 gtg gcc atg gct tcc aac gac aca cct gaa ggg gtg cgg tat att tcc    2193
Val Ala Met Ala Ser Asn Asp Thr Pro Glu Gly Val Arg Tyr Ile Ser
    550                 555                 560 tcc aac gtc tgt ggt cct cac ggg aag tgc aag agt cag tcg gga ggc    2241
Ser Asn Val Cys Gly Pro His Gly Lys Cys Lys Ser Gln Ser Gly Gly
565                 570                 575                 580
```

-continued

```
aaa ttc acc tgt gac tgt aac aaa ggc ttc acg gga aca tac tgc cat       2289
Lys Phe Thr Cys Asp Cys Asn Lys Gly Phe Thr Gly Thr Tyr Cys His
            585                 590                 595 gaa aat att aat gac tgt gag agc aac cct tgt aga aac ggt ggc act       2337
Glu Asn Ile Asn Asp Cys Glu Ser Asn Pro Cys Arg Asn Gly Gly Thr
        600                 605                 610 tgc atc gat ggt gtc aac tcc tac aag tgc atc tgt agt gac ggc tgg       2385
Cys Ile Asp Gly Val Asn Ser Tyr Lys Cys Ile Cys Ser Asp Gly Trp
    615                 620                 625 gag ggg gcc tac tgt gaa acc aat att aat gac tgc agc cag aac ccc       2433
Glu Gly Ala Tyr Cys Glu Thr Asn Ile Asn Asp Cys Ser Gln Asn Pro
630                 635                 640 tgc cac aat ggg ggc acg tgt cgc gac ctg gtc aat gac ttc tac tgt       2481
Cys His Asn Gly Gly Thr Cys Arg Asp Leu Val Asn Asp Phe Tyr Cys
645                 650                 655                 660 gac tgt aaa aat ggg tgg aaa gga aag acc tgc cac tca cgt gac agt       2529
Asp Cys Lys Asn Gly Trp Lys Gly Lys Thr Cys His Ser Arg Asp Ser
                665                 670                 675 cag tgt gat gag gcc acg tgc aac aac ggt ggc acc tgc tat gat gag       2577
Gln Cys Asp Glu Ala Thr Cys Asn Asn Gly Gly Thr Cys Tyr Asp Glu
            680                 685                 690 ggg gat gct ttt aag tgc atg tgt cct ggc ggc tgg gaa gga aca acc       2625
Gly Asp Ala Phe Lys Cys Met Cys Pro Gly Gly Trp Glu Gly Thr Thr
        695                 700                 705 tgt aac ata gcc cga aac agt agc tgc ctg ccc aac ccc tgc cat aat       2673
Cys Asn Ile Ala Arg Asn Ser Ser Cys Leu Pro Asn Pro Cys His Asn
    710                 715                 720 ggg ggc aca tgt gtg gtc aac ggc gag tcc ttt acg tgc gtc tgc aag       2721
Gly Gly Thr Cys Val Val Asn Gly Glu Ser Phe Thr Cys Val Cys Lys
725                 730                 735                 740 gaa ggc tgg gag ggg ccc atc tgt gct cag aat acc aat gac tgc agc       2769
Glu Gly Trp Glu Gly Pro Ile Cys Ala Gln Asn Thr Asn Asp Cys Ser
                745                 750                 755 cct cat ccc tgt tac aac agc ggc acc tgt gtg gat gga gac aac tgg       2817
Pro His Pro Cys Tyr Asn Ser Gly Thr Cys Val Asp Gly Asp Asn Trp
            760                 765                 770 tac cgg tgc gaa tgt gcc ccg ggt ttt gct ggg ccc gac tgc aga ata       2865
Tyr Arg Cys Glu Cys Ala Pro Gly Phe Ala Gly Pro Asp Cys Arg Ile
        775                 780                 785 aac atc aat gaa tgc cag tct tca cct tgt gcc ttt gga gcg acc tgt       2913
Asn Ile Asn Glu Cys Gln Ser Ser Pro Cys Ala Phe Gly Ala Thr Cys
    790                 795                 800 gtg gat gag atc aat ggc tac cgg tgt gtc tgc cct cca ggg cac agt       2961
Val Asp Glu Ile Asn Gly Tyr Arg Cys Val Cys Pro Pro Gly His Ser
805                 810                 815                 820 ggt gcc aag tgc cag gaa gtt tca ggg aga cct tgc atc acc atg ggg       3009
Gly Ala Lys Cys Gln Glu Val Ser Gly Arg Pro Cys Ile Thr Met Gly
                825                 830                 835 agt gtg ata cca gat ggg gcc aaa tgg gat gat gac tgt aat acc tgc       3057
Ser Val Ile Pro Asp Gly Ala Lys Trp Asp Asp Asp Cys Asn Thr Cys
            840                 845                 850 cag tgc ctg aat gga cgg atc gcc tgc tca aag gtc tgg tgt ggc cct       3105
Gln Cys Leu Asn Gly Arg Ile Ala Cys Ser Lys Val Trp Cys Gly Pro
        855                 860                 865 cga cct tgc ctg ctc cac aaa ggg cac agc gag tgc ccc agc ggg cag       3153
Arg Pro Cys Leu Leu His Lys Gly His Ser Glu Cys Pro Ser Gly Gln
    870                 875                 880 agc tgc atc ccc atc ctg gac gac cag tgc ttc gtc cac ccc tgc act       3201
Ser Cys Ile Pro Ile Leu Asp Asp Gln Cys Phe Val His Pro Cys Thr
885                 890                 895                 900
```

-continued

```
ggt gtg ggc gag tgt cgg tct tcc agt ctc cag ccg gtg aag aca aag      3249
Gly Val Gly Glu Cys Arg Ser Ser Ser Leu Gln Pro Val Lys Thr Lys
            905                 910                 915 tgc acc tct gac tcc tat tac cag gat aac tgt gcg aac atc aca ttt      3297
Cys Thr Ser Asp Ser Tyr Tyr Gln Asp Asn Cys Ala Asn Ile Thr Phe
        920                 925                 930 acc ttt aac aag gag atg atg tca cca ggt ctt act acg gag cac att      3345
Thr Phe Asn Lys Glu Met Met Ser Pro Gly Leu Thr Thr Glu His Ile
    935                 940                 945 tgc agt gaa ttg agg aat ttg aat att ttg aag aat gtt tcc gct gaa      3393
Cys Ser Glu Leu Arg Asn Leu Asn Ile Leu Lys Asn Val Ser Ala Glu
950                 955                 960 tat tca atc tac atc gct tgc gag cct tcc cct tca gcg aac aat gaa      3441
Tyr Ser Ile Tyr Ile Ala Cys Glu Pro Ser Pro Ser Ala Asn Asn Glu
965                 970                 975                 980 ata cat gtg gcc att tct gct gaa gat ata cgg gat gat ggg aac ccg      3489
Ile His Val Ala Ile Ser Ala Glu Asp Ile Arg Asp Asp Gly Asn Pro
                985                 990                 995 atc aag gaa atc act gac aaa ata atc gat ctt gtt agt aaa cgt gat      3537
Ile Lys Glu Ile Thr Asp Lys Ile Ile Asp Leu Val Ser Lys Arg Asp
            1000                1005                1010 gga aac agc tcg ctg att gct gcc gtt gca gaa gta aga gtt cag agg      3585
Gly Asn Ser Ser Leu Ile Ala Ala Val Ala Glu Val Arg Val Gln Arg
        1015                1020                1025 cgg cct ctg aag aac aga aca gat ttc ctt gtt ccc ttg ctg agc tct      3633
Arg Pro Leu Lys Asn Arg Thr Asp Phe Leu Val Pro Leu Leu Ser Ser
    1030                1035                1040 gtc tta act gtg gct tgg atc tgt tgc ttg gtg acg gcc ttc tac tgg      3681
Val Leu Thr Val Ala Trp Ile Cys Cys Leu Val Thr Ala Phe Tyr Trp
1045                1050                1055                1060 tgc ctg cgg aag cgg cgg aag ccg ggc agc cac aca cac tca gcc tct      3729
Cys Leu Arg Lys Arg Arg Lys Pro Gly Ser His Thr His Ser Ala Ser
                1065                1070                1075 gag gac aac acc acc aac aac gtg cgg gag cag ctg aac cag atc aaa      3777
Glu Asp Asn Thr Thr Asn Asn Val Arg Glu Gln Leu Asn Gln Ile Lys
            1080                1085                1090 aac ccc att gag aaa cat ggg gcc aac acg gtc ccc atc aag gat tat      3825
Asn Pro Ile Glu Lys His Gly Ala Asn Thr Val Pro Ile Lys Asp Tyr
        1095                1100                1105 gag aac aag aac tcc aaa atg tct aaa ata agg aca cac aat tct gaa      3873
Glu Asn Lys Asn Ser Lys Met Ser Lys Ile Arg Thr His Asn Ser Glu
    1110                1115                1120 gta gaa gag gac gac atg gac aaa cac cag cag aaa gcc cgg ttt gcc      3921
Val Glu Glu Asp Asp Met Asp Lys His Gln Gln Lys Ala Arg Phe Ala
1125                1130                1135                1140 aag cag ccg gcg tac acg ctg gta gac aga gaa gag aag ccc ccc aac      3969
Lys Gln Pro Ala Tyr Thr Leu Val Asp Arg Glu Glu Lys Pro Pro Asn
                1145                1150                1155 ggc acg ccg aca aaa cac cca aac tgg aca aac aaa cag gac aac aga      4017
Gly Thr Pro Thr Lys His Pro Asn Trp Thr Asn Lys Gln Asp Asn Arg
            1160                1165                1170 gac ttg gaa agt gcc cag agc tta aac cga atg gag tac atc gta           4062
Asp Leu Glu Ser Ala Gln Ser Leu Asn Arg Met Glu Tyr Ile Val
        1175                1180                1185 tagcagaccg cgggcactgc cgccgctagg tagagtctga gggcttgtag ttctttaaac    4122
tgtcgtgtca tactcgagtc tgaggccgtt gctgacttag aatccctgtg ttaatttaag    4182
ttttgacaag ctggcttaca ctggca                                         4208
```

<210> SEQ ID NO 7
<211> LENGTH: 1218
<212> TYPE: PRT
<213> ORGANISM: Homo sapiens

<400> SEQUENCE: 7

```
Met Arg Ser Pro Arg Thr Arg Gly Arg Ser Gly Arg Pro Leu Ser Leu
    -30                 -25                 -20

Leu Leu Ala Leu Leu Cys Ala Leu Arg Ala Lys Val Cys Gly Ala Ser
-15                 -10                  -5                  -1   1

Gly Gln Phe Glu Leu Glu Ile Leu Ser Met Gln Asn Val Asn Gly Glu
                 5                  10                  15

Leu Gln Asn Gly Asn Cys Cys Gly Ala Arg Asn Pro Gly Asp Arg
            20                  25                  30

Lys Cys Thr Arg Asp Glu Ser Asp Thr Tyr Phe Lys Val Cys Leu Lys
 35                  40                  45

Glu Tyr Gln Ser Arg Val Thr Ala Gly Pro Cys Ser Phe Gly Ser
 50                  55                  60                  65

Gly Ser Thr Pro Val Ile Gly Gly Asn Thr Phe Asn Leu Lys Ala Ser
                 70                  75                  80

Arg Gly Asn Asp Arg Asn Arg Ile Val Leu Pro Phe Ser Phe Ala Trp
            85                  90                  95

Pro Arg Ser Tyr Thr Leu Leu Val Glu Ala Trp Asp Ser Ser Asn Asp
            100                 105                 110

Thr Val Gln Pro Asp Ser Ile Ile Glu Lys Ala Ser His Ser Gly Met
115                 120                 125

Ile Asn Pro Ser Arg Gln Trp Gln Thr Leu Lys Gln Asn Thr Gly Val
130                 135                 140                 145

Ala His Phe Glu Tyr Gln Ile Arg Val Thr Cys Asp Asp Tyr Tyr Tyr
                150                 155                 160

Gly Phe Gly Cys Asn Lys Phe Cys Arg Pro Arg Asp Asp Phe Phe Gly
            165                 170                 175

His Tyr Ala Cys Asp Gln Asn Gly Asn Lys Thr Cys Met Glu Gly Trp
            180                 185                 190

Met Gly Pro Glu Cys Asn Arg Ala Ile Cys Arg Gln Gly Cys Ser Pro
195                 200                 205

Lys His Gly Ser Cys Lys Leu Pro Gly Asp Cys Arg Cys Gln Tyr Gly
210                 215                 220                 225

Trp Gln Gly Leu Tyr Cys Asp Lys Cys Ile Pro His Pro Gly Cys Val
                230                 235                 240

His Gly Ile Cys Asn Glu Pro Trp Gln Cys Leu Cys Glu Thr Asn Trp
            245                 250                 255

Gly Gly Gln Leu Cys Asp Lys Asp Leu Asn Tyr Cys Gly Thr His Gln
            260                 265                 270

Pro Cys Leu Asn Gly Gly Thr Cys Ser Asn Thr Gly Pro Asp Lys Tyr
275                 280                 285

Gln Cys Ser Cys Pro Glu Gly Tyr Ser Gly Pro Asn Ser Glu Ile Ala
290                 295                 300                 305

Glu His Ala Cys Leu Ser Asp Pro Cys His Asn Arg Gly Ser Cys Lys
                310                 315                 320

Glu Thr Ser Leu Gly Phe Glu Cys Glu Cys Ser Pro Gly Trp Thr Gly
            325                 330                 335

Pro Thr Cys Ser Thr Asn Ile Asp Asp Cys Ser Pro Asn Asn Cys Ser
            340                 345                 350
```

```
His Gly Gly Thr Cys Gln Asp Leu Val Asn Gly Phe Lys Cys Val Cys
355                 360                 365

Pro Pro Gln Trp Thr Gly Lys Thr Cys Gln Leu Asp Ala Asn Glu Cys
370                 375                 380                 385

Glu Ala Lys Pro Cys Val Asn Ala Lys Ser Cys Lys Asn Leu Ile Ala
                390                 395                 400

Ser Tyr Tyr Cys Asp Cys Leu Pro Gly Trp Met Gly Gln Asn Cys Asp
            405                 410                 415

Ile Asn Ile Asn Asp Cys Leu Gly Gln Cys Asn Asp Ala Ser Cys
        420                 425                 430

Arg Asp Leu Val Asn Gly Tyr Arg Cys Ile Cys Pro Pro Gly Tyr Ala
        435                 440                 445

Gly Asp His Cys Glu Arg Asp Ile Asp Glu Cys Ala Ser Asn Pro Cys
450                 455                 460                 465

Leu Asn Gly Gly His Cys Gln Asn Glu Ile Asn Arg Phe Gln Cys Leu
                470                 475                 480

Cys Pro Thr Gly Phe Ser Gly Asn Leu Cys Gln Leu Asp Ile Asp Tyr
                485                 490                 495

Cys Glu Pro Asn Pro Cys Gln Asn Gly Ala Gln Cys Tyr Asn Arg Ala
            500                 505                 510

Ser Asp Tyr Phe Cys Lys Cys Pro Glu Asp Tyr Glu Gly Lys Asn Cys
515                 520                 525

Ser His Leu Lys Asp His Cys Arg Thr Thr Pro Cys Glu Val Ile Asp
530                 535                 540                 545

Ser Cys Thr Val Ala Met Ala Ser Asn Asp Thr Pro Glu Gly Val Arg
                550                 555                 560

Tyr Ile Ser Ser Asn Val Cys Gly Pro His Gly Lys Cys Lys Ser Gln
                565                 570                 575

Ser Gly Gly Lys Phe Thr Cys Asp Cys Asn Lys Gly Phe Thr Gly Thr
            580                 585                 590

Tyr Cys His Glu Asn Ile Asn Asp Cys Glu Ser Asn Pro Cys Arg Asn
595                 600                 605

Gly Gly Thr Cys Ile Asp Gly Val Asn Ser Tyr Lys Cys Ile Cys Ser
610                 615                 620                 625

Asp Gly Trp Glu Gly Ala Tyr Cys Glu Thr Asn Ile Asn Asp Cys Ser
                630                 635                 640

Gln Asn Pro Cys His Asn Gly Gly Thr Cys Arg Asp Leu Val Asn Asp
            645                 650                 655

Phe Tyr Cys Asp Cys Lys Asn Gly Trp Lys Gly Lys Thr Cys His Ser
        660                 665                 670

Arg Asp Ser Gln Cys Asp Glu Ala Thr Cys Asn Asn Gly Gly Thr Cys
675                 680                 685

Tyr Asp Glu Gly Asp Ala Phe Lys Cys Met Cys Pro Gly Gly Trp Glu
690                 695                 700                 705

Gly Thr Thr Cys Asn Ile Ala Arg Asn Ser Ser Cys Leu Pro Asn Pro
            710                 715                 720

Cys His Asn Gly Gly Thr Cys Val Val Asn Gly Glu Ser Phe Thr Cys
            725                 730                 735

Val Cys Lys Glu Gly Trp Glu Gly Pro Ile Cys Ala Gln Asn Thr Asn
        740                 745                 750

Asp Cys Ser Pro His Pro Cys Tyr Asn Ser Gly Thr Cys Val Asp Gly
755                 760                 765
```

-continued

```
Asp Asn Trp Tyr Arg Cys Glu Cys Ala Pro Gly Phe Ala Gly Pro Asp
770                 775                 780                 785

Cys Arg Ile Asn Ile Asn Glu Cys Gln Ser Ser Pro Cys Ala Phe Gly
                790                 795                 800

Ala Thr Cys Val Asp Glu Ile Asn Gly Tyr Arg Cys Val Cys Pro Pro
            805                 810                 815

Gly His Ser Gly Ala Lys Cys Gln Glu Val Ser Gly Arg Pro Cys Ile
        820                 825                 830

Thr Met Gly Ser Val Ile Pro Asp Gly Ala Lys Trp Asp Asp Asp Cys
    835                 840                 845

Asn Thr Cys Gln Cys Leu Asn Gly Arg Ile Ala Cys Ser Lys Val Trp
850                 855                 860                 865

Cys Gly Pro Arg Pro Cys Leu Leu His Lys Gly His Ser Glu Cys Pro
                870                 875                 880

Ser Gly Gln Ser Cys Ile Pro Ile Leu Asp Asp Gln Cys Phe Val His
            885                 890                 895

Pro Cys Thr Gly Val Gly Glu Cys Arg Ser Ser Ser Leu Gln Pro Val
        900                 905                 910

Lys Thr Lys Cys Thr Ser Asp Ser Tyr Tyr Gln Asp Asn Cys Ala Asn
    915                 920                 925

Ile Thr Phe Thr Phe Asn Lys Glu Met Met Ser Pro Gly Leu Thr Thr
930                 935                 940                 945

Glu His Ile Cys Ser Glu Leu Arg Asn Leu Asn Ile Leu Lys Asn Val
                950                 955                 960

Ser Ala Glu Tyr Ser Ile Tyr Ile Ala Cys Glu Pro Ser Pro Ser Ala
            965                 970                 975

Asn Asn Glu Ile His Val Ala Ile Ser Ala Glu Asp Ile Arg Asp Asp
        980                 985                 990

Gly Asn Pro Ile Lys Glu Ile Thr Asp Lys Ile Ile Asp Leu Val Ser
    995                 1000                1005

Lys Arg Asp Gly Asn Ser Ser Leu Ile Ala Ala Val Ala Glu Val Arg
1010                1015                1020                1025

Val Gln Arg Arg Pro Leu Lys Asn Arg Thr Asp Phe Leu Val Pro Leu
                1030                1035                1040

Leu Ser Ser Val Leu Thr Val Ala Trp Ile Cys Cys Leu Val Thr Ala
            1045                1050                1055

Phe Tyr Trp Cys Leu Arg Lys Arg Arg Lys Pro Gly Ser His Thr His
        1060                1065                1070

Ser Ala Ser Glu Asp Asn Thr Thr Asn Asn Val Arg Glu Gln Leu Asn
    1075                1080                1085

Gln Ile Lys Asn Pro Ile Glu Lys His Gly Ala Asn Thr Val Pro Ile
1090                1095                1100                1105

Lys Asp Tyr Glu Asn Lys Asn Ser Lys Met Ser Lys Ile Arg Thr His
                1110                1115                1120

Asn Ser Glu Val Glu Glu Asp Asp Met Asp Lys His Gln Gln Lys Ala
            1125                1130                1135

Arg Phe Ala Lys Gln Pro Ala Tyr Thr Leu Val Asp Arg Glu Glu Lys
        1140                1145                1150

Pro Pro Asn Gly Thr Pro Thr Lys His Pro Asn Trp Thr Asn Lys Gln
    1155                1160                1165

Asp Asn Arg Asp Leu Glu Ser Ala Gln Ser Leu Asn Arg Met Glu Tyr
1170                1175                1180                1185

Ile Val
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthetic
      DNA
<223> OTHER INFORMATION: "n" represents a, t, c, g, other or unknown

<400> SEQUENCE: 8
tgcststgyg anaccaactg                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
tttatktcrc awktckgwcc                                                   20

<210> SEQ ID NO 10
<211> LENGTH: 180
<212> TYPE: DNA
<213> ORGANISM: Homo sapiens

<400> SEQUENCE: 10
gagtgtgcac ctggcttcgc ggggcctgac tgccgcatca acatcgacga gtgccagtcc       60
tcgccctgtg cctacggggc cacgtgtgtg gatgagatca acgggtatcg ctgtagctgc      120
ccacccggcc gagccggccc ccggtgccag gaagtgatcg ggttcgggag atcctgctgg      180

<210> SEQ ID NO 11
<211> LENGTH: 252
<212> TYPE: DNA
<213> ORGANISM: Homo sapiens

<400> SEQUENCE: 11
gcatcaactg ccatatcaac gtcaacgact gtcgcgggca gtgtcagcat gggggcacct       60
gcaaggacct ggtgaacggg taccagtgtg tgtgcccacg gggcttcgga ggccggcatt      120
gcgagctgga acgagacaag tgtgccagca gccctgccA cagcggcggc ctctgcgagg      180
acctggccga cggcttccac tgccactgcc cccagggctt ctccgggcct ctctgtgagg      240
tggatgtcga cc                                                          252

<210> SEQ ID NO 12
<211> LENGTH: 184
<212> TYPE: DNA
<213> ORGANISM: Homo sapiens

<400> SEQUENCE: 12
caacttttcc tgcatctgtg acagtggctt tactggcacc tactgccatg agaacattga       60
cgactgcctg ggccagccct gccgcaatgg gggcacatgc atcgatgagg tggacgcctt      120
ccgctgcttc tgccccagcg gctgggaggg cgagctctgc gacaccaatc caacgactg       180 cctt                                                                   184

<210> SEQ ID NO 13
<211> LENGTH: 20
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 13
gagtgtgcac ctggcttcgc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
ccagcaggat ctcccgaacc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
gcatcaactg ccatatcaac                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
ggtcgacatc cacctcacag                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
caacttttcc tgcatctgtg                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
aaggcagtcg ttgggattgg                                              20

<210> SEQ ID NO 19
<211> LENGTH: 397
<212> TYPE: DNA
<213> ORGANISM: Homo sapiens
```

```
<400> SEQUENCE: 19
atgaggagct gctgatcgag cgagtgtcgc atgccggcat gatcaacccg gaggaccgct       60
ggaagagcct gcacttcagc ggccacgtgg cgcacctgga gctgcagatc cgcgtgcgct      120
gcgacgagaa ctactacagc gccacttgca acaagttctg ccggccccgc aacgactttt      180
tcggccacta cacctgcgac cagtacggca caaggcctg catggacggc tggatgggca       240
aggagtgcaa ggaagctgtg tgtaaacaag ggtgtaattt gctccacggg ggatgcaccg      300
tgcctgggga gtgcaggtgc agctacggct ggcaagggag gttctgcgat gagtgtgtcc      360
cctaccccgg ctgcgtgcat ggcagttgtg tggagcc                                397

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
atgaggagct gctgatcgag                                                   20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
ggctccacac aactgcccat g                                                 21

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
tcgcgggggc aatgcgggcg cagggccggg ggcgccttcc ccggcggctg ctgctgctgc       60

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
cacacgcgca cgtacgtgtc gc                                                22

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: synthetic
      DNA
<221> NAME/KEY: CDS
<222> LOCATION: (1)..(24)
```

```
<400> SEQUENCE: 24 gat tat aaa gat gat gat gat aaa tga                              27
Asp Tyr Lys Asp Asp Asp Asp Lys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: synthetic
      amino acid

<400> SEQUENCE: 25

Asp Tyr Lys Asp Asp Asp Asp Lys
 1               5

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
gctccgggat ccgctccctg                                            20

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
ctcgagcaac ctgtggaaga gccgcccgta aca                             33

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
ctcgagtcat ttatcatcat catctttata atcacctgtg gaagagccgc ccgtaaca   58

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 29
agatctcctg tggaagagcc gcccgtaaca a                               31

<210> SEQ ID NO 30
<211> LENGTH: 58
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 30
ctcgagtcat ttatcatcat catctttata atcctccttg ccggcgtagc gggcctca        58

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
aaggatcccg agggtgtctg ctggaagcca ggctca                                36

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
cctctagagt cgcggccgtc gcactcattt acc                                   33
```

DIFFERENTIATION-SUPPRESSIVE POLYPEPTIDE SERRATE-2 AND METHODS OF USE

The present application is a divisional application of U.S. application Ser. No. 09/855,722, filed on May 16, 2001, now U.S. Pat. No. 6,638,741, which is a divisional application of U.S. application Ser. No. 09/214,278, filed on Jan. 26, 1999, now U.S. Pat. No. 6,291,210, which is a 371 of PCT/JP97/02414, filed Jul. 11, 1997.

BACKGROUND OF THE INVENTION

1. Field of the Invention

This invention relates to a novel bioactive substance which suppresses differentiation of undifferentiated cells.

2. Description of Related Art

Human blood and lymph contain various types of cells and each cell plays important roles. For example, erythrocytes carry oxygen; platelets have hemostatic action; and lymphocytes prevent infection. These various cells originate from hematopoietic stem cells in the bone marrow. Recently, it has been clarified that the hematopoietic stem cells are differentiated to various blood cells, osteoclasts and mast cells by stimulation of various cytokines in vivo and environmental factors. In the cytokines, there have been found, for example, erythropoietin (EPO) for differentiation to erythrocytes; granulocyte colony stimulating factor (G-CSF) for differentiation to leukocytes; and platelet growth factor (mpl ligand) for differentiation to megakaryocytes which are platelet producing cells; and the former two examples have already been clinically applied.

The differentiated blood cells are generally classified into two groups consisting of blood precursor cells which are destined to differentiate to specific blood series and hematopoietic stem cells which have differentiation ability to all series and self-replication activity. The blood precursor cells can be identified by various colony assays; however, an identification method for the hematopoietic stem cells have not been established. In these cells, stem cell factor (SCF), interleukin-3 (IL-3), granulocyte-macrophage colony stimulating factor (GM-CSF), interleukin-6 (IL-6), interleukin-1 (IL-1), granulocyte colony stimulating factor (G-CSF) and oncostatin M have been reported to stimulate cell differentiation and proliferation.

Trials for expansion of hematopoietic stem cells in vitro have been conducted in order to replace bone marrow transplantation for applying hematopoietic stem cell transplantation therapy or gene therapy. However, when the hematopoietic stem cells are cultured in the presence of the above mentioned cytokines, multi-differentiation activities and self-replication activities, which are originally in the position of the hematopoietic stem cells, gradually disappeared and are changed to the blood cell precursors which only differentiate to specific series after 5 weeks of cultivation, and multi-differentiation activity, which is one of the specific features of the hematopoietic stem cells, is lost (Wanger et al. Blood 86, 512–523, 1995).

For proliferation of the blood precursor cells, a single cytokine is not sufficient, but rather the synergistic action of several cytokines is important. Consequently, in order to proliferate the hematopoietic stem cells while maintaining the specific features of the hematopoietic stem cells, it is necessary to add cytokines which suppress differentiation together with the cytokines which proliferate and differentiate the undifferentiated blood cells. In general, many cytokines which stimulate proliferation or differentiation of cells are known, but few cytokines which suppress cell differentiation are known. For example, leukemia inhibitory factor (LIF) has an action of proliferation of mouse embryonic stem cells without differentiation, but it has no action against the hematopoietic stem cells or blood precursor cells. Transforming growthfactor (TGF-β) has suppressive action for proliferation against various cells, but has no fixed actions against the hematopoietic stem cells or blood precursor cells.

Not only blood cells but also undifferentiated cells, especially stem cells, are thought to be involved in tissue regeneration. These regeneration of tissues and proliferation of undifferentiated cells in each tissue can be applied in various known ways (Katsutoshi Yoshizato, Regenration—a mechanism of regeneration, 1966, Yodosha Publ. Co.).

Notch is a receptor type membrane protein involved in regulation of nerve cell differentiation found in *Drosophia*. Homologues of Notch are found in various invertebrates and vertebrates including nematoda (Lin-12), *Xenopus laevis* (Xotch), mouse (Motch) and human (TAN-1).

Ligands of Notch in *Drosophila* are known. These are *Drosophila* Delta (Delta) and *Drosophila* Serrate (Serrate). Notch ligand homologues are found in various animals similar to those of Notch receptors (Artavanis-Tsakonas et al., Science 268, 225–232, 1995).

Human Notch homologue, TAN-1 is found widely in the tissues in vivo (Ellisen et al., Cell 66, 649–661, 1991). Two Notch analogous molecules other than TAN-1 have been reported (Artavanis-Tsakonas et al., Science 268, 225–232, 1995). Expression of TAN-1 was also observed in CD34 positive cells in blood cells by PCR (Polymerase Chain Reaction) (Milner et al., Blood 83, 2057–2062, 1994). However, in relation to humans, gene cloning of human Delta and human Serrate, which are thought to be Notch ligand, has not been reported.

In *Drosophila* Notch, binding with the ligand was studied and investigated in detail, and it was found that the Notch can be bound to the ligand with Ca++ at the binding region, which is a repeated amino acid sequence No. 11 and No. 12 in the amino acid sequence repeat of Epidermal Growth Factor (EGF) (Fehon et al., Cell 61, 523–534, 1990, Rebay et al., ibid. 67, 687–699, 1991 and Japan. Patent PCT Unexam. Publ. 7-503123). EGF-like repeated sequences are conserved in Notch homologues of other species. Consequently, the same mechanism in binding with ligand is assumed.

An amino acid sequence which is called DSL (Delta-Serrate-Lag-2) near the amino acid terminal, and EGF-like repeated sequence like in the receptor are conserved in the ligand (Artavanis-Tsakonas et al., Science 268, 225–232, 1995). EGF-like sequence has been found in thrombomodulin (Jackman et al., Proc. Natl. Acad. Sci. USA 83, 8834–8838, 1986), low density lipoprotein (LDL) receptor (Russell et al., Cell 37, 577–585, 1984), and blood coagulating factor (Furie et al., Cell 53, 505–518,1988), and is thought to play important roles in extracellular coagulation and adhesion.

The vertebrate homologues of the cloned *Drosophila* Delta were found in chicken (C-Delta-1) and *Xenopus laevis* (X-Delta-1), and it has been reported that X-Delta-1 had acted through Xotch in the generation of the protoneuron (Henrique et al., Nature 375, 787–790, 1995 and Chitnis et al., ibid. 375, 761–766, 1995).

A vertebrate homologue of *Drosophila* Serrate was found in rat as rat Jagged (Jagged) (Lindsell et al., Cell 80, 909–917, 1995). According to Lindsell et al., mRNA of the rat Jagged is detected in the spinal cord of fetal rats. As a result of cocultivation of a myoblast cell line that is forced to over express rat Notch with a rat Jagged expression cell line, suppression of differentiation of the myoblast cell line is found. However, the rat Jagged has no action against the myoblast cell line without forced expression of the rat Notch.

Considering the above reports, Notch and ligand thereof may be involved in differentiation regulation of the nerve cells; however, except for some myoblast cells, their actions against cells including blood cells, especially primary cells, are unknown.

As mentioned above, concerning undifferentiated cells, proliferation while maintaining their specificities has not been performed. Major reasons are that factors suppressing differentiation of the undifferentiated cells have not been sufficiently identified.

SUMMARY AND OBJECTS OF THE INVENTION

A principal object of the present invention is to provide a compound originated from novel factors which can suppress differentiation of undifferentiated cells.

We have set up a hypothesis that the Notch and its ligand have an action of differential regulation not only for neurogenic cells but also for various undifferentiated cells. However, in case of clinical application in humans, prior known different species such as chicken or Xenopus laevos type Notch ligand have species-previously specific problems and anti-genicities. Consequently, to obtain prior unknown human Notch ligand is essentially required. We had an idea that ligands of the human Notch (TAN-1 etc.), which are a human Delta homologue (hereinafter designated as human Delta) and human Serrate homologue (hereinafter designated as human Serrate), may be found. Also we had an idea that these findings may be a candidate for drugs useful for differential regulation of the undifferentiated cells. We have tried to discover the same.

In order to discover human Notch ligands, we have analyzed amino acid sequences which are conserved in animals other than humans, and tried to discover genes by PCR using mixed primers of the corresponding DNA sequence. As a result of extensive studies, we have succeeded in isolation of cDNAs coding amino acid sequences of two new molecules, novel human Delta-1 and novel human Serrate-1, and have prepared protein expression systems having various forms using these cDNAs. Also we have established a purification method of the proteins which were purified and isolated, and already filed a patent application therefor (International Publication WO 97/19172).

Furthermore, we have tried to discover *Drosophila* Delta and Serrate analogous molecules other than human Delta and human Serrate (hereinafter designated as human Delta-1 and human Serrate-1, respectively) of the above patent application in vertebrates.

We have tried to search on the data base of genetic sequences. Namely, based on the human Serrate-1 genetic sequence (amino acids sequence in SEQ ID NO: 5) which was at first discovered by us, we have found several numbers of gene fragments (length with 200–350 bp) with highhomology from EST (Expressed Sequence Tag), which is a data of gene fragments of random human cDNA sequence in the gene sequence data base GenBank, using a gene sequence search software Genetyx/CD (Software Development Co.).

These short length gene fragments were cloned by PCR, and these gene fragments were used as probes to try cloning of the longer length gene fragments from human fetal cDNA libraries. The thus isolated longer gene fragments, of which the genetic sequences were determined, were again compared with genetic sequence of human Serrate-1. As a result, a gene, which has relatively high homology with human Serrate-1, is identified and is designated as human Serrate-2. The full length of Serrate-2 gene was isolated successfully.

Furthermore, expression vectors of the said cloned Serrate-2 were constructed. A purification method of these proteins was established and the said protein was purified and isolated. Antibodies against human Serrate-2 are prepared using the said human Serrate-2, and a purification method of the said antibodies was established, then the activity against undifferentiated blood cells was confirmed. The present invention was completed accordingly.

The present invention relates to a polypeptide comprising amino acid sequence of SEQ ID NO: 1, 2 or 3 of the sequence listing and the polypeptide having differentiation suppressive action against undifferentiated cells. Furthermore, the undifferentiated cells are undifferentiated cells except for those of the brain and nervous system or muscular system cells, and in which the undifferentiated cells are undifferentiated blood cells. The present invention also relates to polypeptides having growth inhibitory action against vascular endothelial cells, a pharmaceutical composition containing the said polypeptides, a cell culture medium containing the said polypeptides and a cell culture medium in which the cells are undifferentiated blood cells.

The present invention furthermore relates to a DNA coding a polypeptide comprising amino acid sequence of SEQ ID NO: 1, 2 or 3 of the sequence listing, the DNA having DNA sequence 90–731 DNA sequence 90–3254, or DNA sequence 90–3725 of SEQ ID NO: 4 of the sequence listing. The present invention still further relates to a recombinant DNA made by ligating a DNA coding a polypeptide comprising amino acid sequence of SEQ ID NO: 1, 2 or 3 and a vector DNA which can express in the host cell and a cell comprising transformed by the recombinant DNA.

The present invention also relates to a process for production of polypeptides by culturing cells and isolating the thus produced compounds, and an antibody specifically recognizing the polypeptide having the amino acid sequence of SEQ ID NO. 1, 2 or 3 of the sequencing listing.

DETAILED DESCRIPTION OF PREFERRED EMBODIMENTS

The present invention is explained in detail in the following.

Preparation of cDNA necessary for gene manipulation, expression analysis by Northern blotting, screening by hybridization, preparation of recombinant DNA, determination of DNA base sequence and preparation of cDNA library, all of which are series of molecular biological experiments, can be performed according to a description of the conventional textbook for the experiments. The above conventional textbook of the experiments is, for example, Maniatis et al. ed. Molecular Cloning, A laboratory manual, 1989, Eds., Sambrook, J., Fritsch, E. F. and Maniatis, T., Cold Spring Harbor Laboratory Press.

A novel compound of the present invention has at least polypeptides in the sequence listing SEQ ID NO: 1–3. Mutants and alleles which naturally occur in nature are included in the polypeptide of the present invention unless the polypeptides of the sequence listing, SEQ ID NO: 1, 2 or 3 lose their properties. Modification and substitution of amino acids are described in detail in the patent application by the name of Bennet et al. (National Unexam. Publ. WO 96/2645) and can be performed according to the description thereof. A modified polypeptide in the present invention means the modified polypeptide prepared by these amino acid replacements and is defined as amino acid sequences having identity of more than 90% in its amino acid sequence.

A DNA sequence coding polypeptides of the sequence listing, SEQ ID NO: 1–3 is shown in the sequence listing, SEQ ID NO: 4 as well as its amino acid sequence. In these DNA sequences, even if an amino acid level mutation is not generated, naturally isolated chromosomal DNA or cDNA thereof may have a possibility to mutate in the DNA base sequence as a result of degeneracy of the genetic code without changing amino acid sequence coded by the DNA. A 5'-untranslated region and 3'-untranslatedregion are not involved in amino acid sequence determination of the polypeptide, so the DNA sequences of these regions are easily mutated. The base sequence obtained by these degeneracies of the genetic codes is included in the DNA of the present invention.

Undifferentiated cells in the present invention are defined as cells which can grow by specific stimulation, and cells which can be differentiated to cells having specific functions as a result of specific stimulations. These include undifferentiated cells of the skin tissues, undifferentiated blood cells and nervous systems, undifferentiated cells of the muscular systems and undifferentiated blood cells. These cells include those having self-replication activity which are called stem cells, and those having an ability to generate the cells of these lines. The differentiation-suppressive action means suppressive action for autonomous or heteronomous differentiation of the undifferentiated cells, and is an action for maintaining the undifferentiated condition. The brain and nervous undifferentiated cells can be defined as cells having an ability to differentiate to the cells of the brain or nerve having specific functions by specific stimulation. The undifferentiated cells of the muscular systems can be defined as cells having an ability to differentiate to the muscular cells having specific functions by specific stimulation. The blood undifferentiated cells in the present invention can be defined as cell groups consisting of the blood precursor cells which are differentiated to the specific blood series identified by blood colony assay, and hematopoietic stem cells having differentiation to every series and self-replication activities.

In the sequence listing, the amino acid sequence in SEQ ID NO: 1 is a sequence of the active center of the present invention of human Serrate-2 minus the signal peptide, and corresponds to an amino acid No. 1 to 217 in SEQ ID NO: 3 of the mature full length amino acid sequence of human Serrate-2 of the present invention. The amino acid sequence in SEQ ID NO:2 is amino acid sequence of extracellular domain of the present invention of human Serrate-2 minus the signal peptide, and corresponds to an amino acid No. 1 to 1058 in SEQ ID NO: 3 of the mature full length amino acid sequence of human Serrate-2 of the present invention. The amino acid sequence of SEQ ID NO: 3 is the mature full length amino acid sequence of the human Serrate-2 of the present invention. The sequence of SEQ ID NOS: 4 and 5 is total amino acid sequence of human Serrate-2 of the present invention and cDNA coding the same. The sequence of SEQ ID NOS: 6 and 7 is total amino acid sequence of human Serrate-1 used in the present invention and cDNA coding the same.

The left and right ends of the amino acid sequences in the sequence listings indicate amino terminal (hereinafter designates as N-terminal) and carboxyl terminal (hereinafter designates as C-terminal), respectively, and the left and right ends of the nucleotide sequences are 5'-terminal and 3'-terminal, respectively.

Cloning of human Notch ligand gene can be performed by the following method. During the evolution of the organisms, a part of the amino acid sequences of the human Notch ligand is conserved. DNA sequence corresponding to the conserved amino acid sequence is designed, and is used as a primer of RT-PCR (Reverse Transcription Polymerase Chain Reaction), then a PCR template of human origin is amplituded by PCR reaction, whereby fragments of human Notch ligand can be obtained. Furthermore, RT-PCR primer is prepared by applying the known DNA sequence information of the Notch ligand homologue of the organisms other than humans, and the known gene fragments can be possibly obtained from a PCR template of the said organisms.

In order to perform PCR for obtaining fragments of human Notch ligand, PCR for DSL sequence was considered, but a large number of combinations of DNA sequence corresponding to amino acid sequence conserved in this region can be expected, and a design for PCR is difficult. As a result, PCR of the EGF-like sequence has to be selected. As explained above, since EGF-like sequence is conserved in a large number of molecules, to obtain the fragments and identification are extremely difficult. We have designed and prepared about 50 PCR primer sets, for example the primer set of the sequence shown in Referential example 1, and PCR was performed with these primer sets by using PCR template of cDNA prepared from poly A+RNA of various tissues of human origin, and more than 10 PCR products from each tissue were subcloned, as well as performing sequencing for more than 500 types. A clone having a desired sequence of human Serrate-1 could be identified.

Namely, as shown in Reference example 1, the obtained PCR product is cloned in the cloning vector, transforming the host cells by using recombinant plasmid which contains the PCR product, culturing the host cells containing the recombinant plasmid on a large scale, purifying and isolating the recombinant plasmid, checking the DNA sequence of PCR product which is inserted into the cloning vector, and trying to obtain the gene fragment which may have a sequence of human Serrate-1 by comparing with the sequence of the known Serrate homologue of other species. We have succeeded in discovering a the gene fragment which contains a part of cDNA of human Serate-1, the same sequence of DNA sequence from 1272 to 1737 described in the sequence listing, SEQ ID NO: 6. As shown in Referential example 2, using the thus obtained human Serrate-1 gene fragment, full length cDNA is obtained from human cDNA library. We have already filed a patent application with these inventions (WO 97/19172).

In the present invention, there may be possibly to exist ligands other than this human Serrate-1 molecule, gene fragments showing high homology in relation to the ligand to the gene sequence coding amino acid sequence of human Serrate-1 molecule, i.e. DNA sequence from 409 to 4062 in the sequence listing SEQ ID NO: 6, are screened in the data base of DNA sequence. Screening was performed by using gene sequence search software Genetyx/CD (software Development Co.) on the DNA/fragments of random human cDNA sequence data base EST (Expressed Sequence Tag) of Genbank (release 91, 1995).

Recently, DNA sequencing technology has progressed, and analysis of total geneomic DNA and full cDNA sequence of humans, nematoda, Arabidopsisthaliana Heynh, etc. were tried by random sequencing of genomic DNA and cDNA (Genome Directory, Nature, 377, 3S, 1995). In the human cDNA, EST project of TIGR (The Institute for Genomic Research), EST project of Washington Univ.—Merck, STS project of Colorad Univ. joined in these projects. Partial base sequences of cDNA provided by these organizations are registered in DNA database of Genbank and EMBL and are disclosed. According to Genbank release 91 of October, 1995, cumulative registered numbers of EST clone are about 330,000 clones with average length 346 bp.

Based on data in these databases, gene sequences or amino acid sequences of known or namely cloned novel molecules are searched by homology search. Possibility of existence of the analogues or similar family molecules of these molecules can be known and the sequence information of the partial DNA sequence can be obtained.

For analysis, commercially available analysis software can be used, or analysis software attached to the database, for example BLAST of Genbank can be used. By using these, analysis can be performed by accessing to National Center of Biotechnology Information, U.S.A., Institute of Chemistry, Kyoto Univ., Japan, through WWW (world wide webb) or E-mail.

Gene sequence information of gene fragments (about 200–350 bp) with high similarity to the target gene can be obtained through these operations. The information of the obtained gene fragment includes general gene sequence information together with clone name of the gene and organs or tissues in which the gene was extracted. In the information on DNA sequence, this is essentially raw data obtained by DNA sequence, including unknown DNA sequences with marked "n", and incorrect DNA sequence information. Consequently, this DNA sequence information is not always exact.

From this gene information, DNA sequences without unknown residues N are thought to be highly probable DNA sequence information. Further the most probable DNA sequences within these DNA sequences are compared and DNA fragments having significant homology are identified in this region (in case of a gene with 200 bases, similarity of DNA sequence above 40% is preferable). The thus identified DNA fragment can be obtained from Genom System Inc., U.S.A. etc., if the name of the clone is known; however, because of knowing disclosed origin of organs, it can be also isolated by PCR from cDNA of commercially available expression organs.

The thus found gene information is partial information, and unless total information is obtained, a full length amino acid sequence, which may be encoded by the said partial sequence of gene, is not always analogous similar molecule used in the original homology search. Exact information about the molecule cannot be shown only by that information. As shown below, we have prepared a number of probes having homology and performed cloning by plaque hybridization; however, most DNA fragments did not code the desired molecules. Consequently, this technique may be theoretically possible but is not easy technology.

We have prepared probes from about 50 DNA fragments which showed similarity with human Serrate-1 cDNA by PCR. Finally, as shown in the following, cloning was performed by library screening technique. As a result of determining the DNA sequence, a gene isolated by using 3 types of DNA probes having sequence of SEQ ID NOS: 10, 11 and 12, which were prepared based on DNA sequence clones registered in Genbank (Reg. No. T08853, R50026 and R46751) as described in Example 1, is a DNA fragment coding human Serrate-2 molecule.

Furthermore, using the thus isolated cDNA fragment as a probe and screening a cDNA library of the expression organs, then the longer gene having DNA sequence or full length cDNA gene can be screened. The full length cloning can be made by isotope labelling and non-isotope labelling with the partial cloning gene, and screening the library by hybridization or other method. Isotope labelling can be performed by, for example, terminal labelling by using [3 2 P] γ-ATP and T4 polynucleotide kinase, or other labelling methods such as nick translation or primer extension method can be applied.

Furthermore, cloning of the full length gene or longer gene fragments can be performed by methods for extension of gene sequence with 5'-RACE or 3'-RACE method without using a library. In other methods, human origin cDNA library is ligated into the expression vector, expressing by COS-7 or other cells, the ligated molecule is searched using receptor Notch protein and the objective gene is screened by expression cloning to isolate cDNA of the ligand. In the expression cloning, a cell sorter fractionation method which is applied with binding with polypeptide containing amino acid sequence of prior known 4 Notches such as TAN-1, and a detection method by film emulsion using radioisotope can be-mentioned.

In this specification, a method for obtaining genes of human Serrate-2 is explained, and various methods clearly shown in this invention including PCR, by which clonings of human Delta-1 and human Serrate-1 were performed, can be applied for obtaining new Notch ligand family molecules which have never been cloned. For example, the conserved domains are found by comparison with amino acid sequence or DNA sequence of human Serrate-1 or human Serrate-2, and cloning thereof is performed after applying PCR, and also cloning can be performed by searching EST based on human Delta-1 or human Serrate-2. These cloned new Notch ligand family molecules can be used as the same human Serrate-2 shown in the present invention, for example by full length cloning, preparating expression vector, preparation of transformed cells, protein production, antibody production or screening the bioactive substances, and differentiation suppressive action for cells can be expected.

As shown in Example 2, these three gene fragments are labelled with radioisotope to prepare hybridization probes, screened using cDNA of human fetal brain origin as the screening library, whereupon the DNA sequence of the thus obtained clones is determined, and found to be highly similar with human Serrate-1 in full length of DNA nucleotide sequence. In these screenings, a full length cDNA sequence encoding a full length amino acids sequence cannot be cloned. A further DNA probe is prepared based on the cloned DNA sequence, and again screening is performed, but the full length gene cannot be identified. Finally, gene cloning containing the translation initiation Met codon is performed by 5'-RACE method, the DNA sequence is determined and finally we succeeded in cloning of cDNA encoding full length of gene sequence of human Serrate-2. The thus cloned cDNA was ligated as shown in Example 2 and cDNA encoding the full length of the said human Serrate-2 can be obtained.

Examples of plasmids integrated with cDNA are, for example, *E. coli* originated pBR322, pUC18, pUC19, pUC118 and pUC119 (Takara Shuzo Co., Japan), but other plasmids can be used if they replicate and proliferate in the host cells. Examples of phage vectors integrated with cDNA are, for example, λgt10 and λgt11, but other vectors can be used if they can grow in the host cells. The thus obtained plasmids are transduced into suitable host cells such as genus *Escherichia* and genus *Bacillus* using calcium chloride method. Examples of the above genus Escherichia are

*Escherichia coli* K12HB101, MC1061, LE392, JM109. Examples of the above genus *Bacillus* is *Bacillus subtilis* MI114. Phage vector can be introduced into the proliferated *E. coli* by the in vitro packaging method (Proc. Natl. Acad. Sci., 71: 2442, 1978).

The cloned full length DNA sequence was compared with the database (Genbank release 93, 1996), and it was found that the total sequence is a novel sequence, although there are partially the previously mentioned three EST clones and several EST clone data as non-identical partial sequences other than those three EST clones.

Furthermore, the said amino acid sequence of human Serrate-2, i.e. amino acid sequences in SEQ ID NO: 1, 2 and 3, were compared with the database of the prior known amino acid sequence (SWISS-PROT, release 32, 1995 and Genbank CDS, release 93, 1996), and found that there are no identical amino acid sequences and that these are novel sequences. According to a comparison in amino acid sequence of human Serrate-1 and Serrate homologue of the other organisms, the homologies with human Serrate-1, *Drosophila* Serrate, and rat jagged are 53.1%, 34.3%, and 52.3%, respectively. The substance of the present invention is different from these substances and is a novel substance having new amino acid sequences and is first discovered by the present inventors.

The amino acid sequence was analyzed in hydrophilic part and hydrophobic part according to a method by Kyte-Doolittle (J. Mol. Biol., 157: 105, 1982). Results indicate that in the amino acid sequence listed in SEQ ID NO: 5, amino acid sequence of a precursor of full length gene consists of 1238 amino acids residue from −26 to 1212 in amino acid sequence, and the signal peptide domain is estimated to correspond amino acid sequence of 26 amino acids residue from No. −26 methionine to No. −1 proline; extracellular domain: 1055 amino acids residue from No. 1 methionine to No. 1055 glycine; transmembrane domain: 24 amino acids residue from No. 1056 leucine to No. 1079 tryptophane; and intracellualr domain: region from No. 1080 threonine to No. 1212 glutamate. These domains are the estimated domain construction from the amino acid sequence, and the actual form may differ from the above structure, and the constituent amino acids of each domain hereinabove defined may change 5 to 10 amino acids per sequence.

In the amino terminal (N-terminal), as shown in Example 6, identification of N-terminal amino acid sequence of the purified ligand polypeptides EXS2Fc and EXS2FLAG of the present invention was performed and found that it was methionine of No. 1 in SEQ ID NO: 1–3. Consequently, signal peptide is at least from −26 methionine to −1 proline in SEQ ID NO: 5.

The family molecules of Notch ligand in relation to extracelluar domain have evolutionally conserved common sequence, i.e. DSL sequence and repeated EGF-like sequence. As a result of comparison with amino acid sequence of human Serrate-2 and human Serrate-1, the conserved sequence is estimated from amino acid sequence Serrate-2. Namely, DSL sequence corresponds to the 43 amino acid residue from No. 72 cysteine to No. 214 cysteine of the amino acid sequence in the sequence listing, SEQ ID NO: 5.

EGF-like sequence exists with 16 repeats wherein, in the amino acid sequence in the sequence listing, SEQ ID NO: 5, the first EGf-like sequence from No. 217 cysteine to No. 247 cysteine; the second EGF-like sequence from No. 250 cysteine to No. 278 cysteine; the third EGF-like sequence from No. 285 cysteine to No. 318 cysteine; the fourth EGF-like sequence from No. 325 cysteine to No. 356 cysteine; the fifth EGF-like sequence from No. 363 cysteine to No. 394 cysteine; the sixth EGF-like sequence from No. 401 cysteine to No. 432 cysteine; the seventh EGF-like sequence from No. 439 cysteine to No. 469 cysteine; the eighth EGF-like sequence from No. 476 cysteine to No. 507 cysteine; the ninth EGF-like sequence from No. 514 cysteine to No. 545 cysteine; the 10th EGF-like sequence from No. 563 cysteine to No. 607 cysteine; the 11th EGF-like sequence from No. 614 cysteine to No. 645 cysteine; the 12th EGF-like sequence from No. 652 cysteine to No. 683 cysteine; the 13th EGF-like sequence from No. 690 cysteine to No. 721 cysteine; the 14th EGF-like sequence from No. 729 cysteine to No. 760 cysteine; the 15th EGF-like sequence from No. 767 cysteine to No. 798 cysteine; and the 16th EGF-like sequence from No. 805 cysteine to No. 836 cysteine.

On these cysteine residues, there are 2 cysteine residues between the 9th EGF-like sequence and the 10th EGF-like sequence. Also there are 6 cysteine residues to the direction of N-terminal of DSL sequence and 16cysteine residues to the direction of C-terminal in the 16th EGF-like sequence. These cysteine residues including EGF-like sequence are conserved in almost the same position of the human Serrate-1.

A part for sugar chain attachment is estimated from amino acid sequence of the human Serrate-2 as No. 127, 544, 593, 726 and 1032 asparagine residue in the sequence listing, SEQ ID NO: 3 as a possible binding site of N-glycoside bonding for N-acetyl-D-glycosamine. O-glycoside bond of N-acetyl-D-galactosamine is estimated to be a serine or threonine residue rich part. Protein bound with sugar chain is generally thought to be stable in vivo and to have strong physiological activity. Consequently, in the amino acid sequence of polypeptide having sequence of the sequence listing, SEQ ID NO: 1, 2 or 3, polypeptides having N-glucoside or O-glucoside bond with sugar chain of N-acetyl-D-glucosamine or N-acetyl-D-galactosamine is included in the present invention.

As a result of studies on binding of *Drosophila* Notch and its ligand, amino acid region necessary for binding with ligand of *Drosophila* Notch with the Notch is from N-terminal to DSL sequence of the mature protein, in which signal peptide is removed (Japan. Pat. PCT Unexam. Publ. No. 7-503121). Furthermore, as a result of the similar studies, a study using nematoda by Fitzgerald and Greenwald (Development, 121, 4275–4282, 1995) clearly indicated that full length of Notch ligand-like molecule APX-1 from amino terminal to DSL domain was sufficient length for activation of Notch-like receptor. These facts indicate that a domain necessary for expression of ligand action of human Serrate-2 molecule is a novel amino acid sequence of the sequence listing, SEQ ID NO: 1.

Northern blotting can be performed by using DNA encoding a part or all of gene sequence in the sequence listing, SEQ ID NO: 4. Consequently, a method for detection of expression of these genes can be achieved by applying with hybridization or PCR by using complementary nucleic acids of above 12mer or above 16mer, preferably above 18mer having nucleic acid sequence of a part of sequence in the sequence listing SEQ ID NO: 4, i.e. antisense DNA or antisense RNA, its methylated, methylphosphated, deaminated, or thiophosphated derivatives. By the same method, detection of homologues of the gene of other organisms such as mice or gene cloning can be achieved.

Further cloning of genes in the genome including humans can be made. Using these genes cloned by such like methods, further detailed functions of the human Serrate-2 of the present invention can be identified. For example, using the modern gene manipulation techniques, every method including transgenic mouse, gene targeting mouse or double knockout mouse in which genes relating to the gene of the present invention are inactivated, can be applied. If abnormalities in the genome of the present gene is found, application to gene diagnosis and gene therapy can be made.

As described in Example 3, an expression in normal human tissues is observed in many tissues, and length of the expressed mRNA is one type of the mRNA with about 5 kb length. This means tjat detecting the expression of mRNA of the said molecule can be applied for diagnosis or detection of malignant tumors in the part of normal organs in which expression of these mRNA cannot be observed. Furthermore, by referring to patterns of the expressed organs, use of human Serrate-2, for which concrete use is not indicated in the present invention, can be found.

A transformant in which vector pUCSR-2, which contains cDNA coding total amino acid sequence of human Serrate-2 of the present invention, is transformed into E. coli JM109, has been deposited in the National Institute of Bio-science and Human-Technology, Agency of Industrial Science and Technology, MITI, of 1-1-3, Higashi, Tsukuba-shi, Ibaragi-ken, Japan. as E. coli: JM109-pUCsr-2. Date of deposit was Oct. 28, 1996, and deposition No. is FERM BP-5727.

Expression and purification of various forms of human Serrate-2 using cDNA coding amino acid sequence of human Serrate-2 isolated by the above methods are known in the literature (Kriegler, Gene Transfer and Expression-A Laboratory Manual Stockton Press, 1990 and Yokota et al. Biomanual Series 4, Gene transfer and expression and analysis, Yodosha Co., 1994). A cDNA coding the amino acid sequence of the isolated said humanSerrate-2 is ligated to preferred expression vector and is produced in the host cells of eukaryotic cells such as animal cells and insect cells or prokaryotic cells such as bacteria.

In the expression of the molecule of the present invention, DNA encoding a polypeptide of the present invention may have the translation initiation condon in 5'-terminal and translation termination codon in 3'-terminal. These translation initiation codon and translation termination codon can be added by using preferred synthetic DNA adapter. Furthermore, for expression of the said DNA, promoter is linked upstream of the DNA sequence. Examples of vector are plasmid originated from Bacillus, plasmid originated from yeast or bacteriophage such as λ-phage and animal virus such as retrovirus and vaccinia virus.

Examples of promoters used in the present invention are any promoters suitable for corresponding to the host cells used in gene expression.

In case that the host cell in the transformation is genus Escherichia, tac-promoter, trp-promoter and lac-promoter are preferred, and in case of host of genus Bacillus, SPO1 promoter and SPO2 promoter are preferred, and in case of host of yeast, PGK promoter, GAP promoter and ADH promoter are preferred.

In case that the host cell is animal cells, a promoter originated from SV40, promoter of retrovirus, metallothionein promoter and heatshock promoter can be applied.

Expression of the polypeptide of the present invention can be effected by using only DNA encoding the amino acid sequence of the sequence listing, SEQ ID NO: 1, 2 or 3. However, a protein having an additional specific function can be produced by using DNA, to which is added cDNA encoding the known antigen epitope for easier detection of the produced polypeptide or to which is added cDNA encoding the immunoglobulin Fc for forming a multimer of the said human Serrate-2.

As shown in Example 4, we have prepared expression vectors, which express extracellular proteins, as follow.

1) DNA encoding the amino acids from No. 1 to 1055 in amino acid sequence in the sequence listing, SEQ ID NO: 2.

2) DNA encoding chimera protein to which added polypeptide having 8 amino acid, i.e. an amino acid sequence consisting of Asp Tyr Lys Asp Asp Asp Asp Lys (hereinafter designates FLAG sequence, the sequence listing, SEQ ID NO: 25), in the C-terminal of the amino acids from No. 1 to 1055 in amino acid sequence in the sequence listing, SEQ ID NO: 2, and 3) DNA encoding chimera protein to which is added Fc sequence below the hinge region of human IgG1 (refer to International Patent Unexam. Publ. WO 94/02053) in the C-terminal of the amino acids from No. 1 to 1055 in amino acid sequence in the sequence listing, SEQ ID NO: 2, and to have dimer structure by disulfide bond in the hinge region, are ligated individually with the expression vector pMKIT-Neo (Maruyama et al., Japan Molecular Biology Soc. Meeting Preliminary lecture record, obtainable from Dr. Maruyama in Tokyo Medical and Dental College) to prepare extracellular expression vectors of human Serrate-1.

The expression vectors, which expresses full-length protein, can be prepared as follows.

4) DNA encoding amino acids from No. 1 to 1212 in the sequence listing, SEQ ID NO: 3 and 5) DNA encoding chimera protein to which is added polypeptide having FLAG sequence in the C-terminal of amino acids from No. 1 to 1212 in the sequence listing, SEQ ID NO: 3 re ligated individually with the expression vector pMKITNeo to prepare the full-length expression vector of human Serrate-2. The transformation is prepared by using expression plasmid containing DNA encoding the thus constructed said human Serrate-2.

Examples of the host are genus Escherichia, genus Bacillus, Yeast and animal cells. Examples of animal cells are simian cell COS-7 and Vero, Chinese hamster cell CHO and silk worm cell SF9.

As shown in Example 5, the above 5 type expression vectors are transduced individually; the human Serrate-2 is expressed in COS-7 cell (obtainable from the Institute of Physical and Chemical Research, Cell Development Bank, RCB0539); and the transformants which were transformed by these expression plasmids, can be obtained. Furthermore, human Serrate-2 polypeptide can be produced by culturing the transformants under suitable culture conditions in medium by known culture methods.

The human Serrate-2 polypeptide can be isolated and purified from the above cultured mass, in general, by the following methods.

For extraction of the substance from cultured microbial cells or cells, microbial cells or cells are collected by known method such as centrifugation after the cultivation, suspended in siutable buffer solution, whereafter the microbial cells or cells are disrupted by means of ultrasonication, lysozyme and/or freeze-thawing and a crude extract of human Serrate-2 protein is collected by centrifugation or filtration. The buffer solution may contain protein-denaturing agents such as urea and guanidine hydrochloride or surface active agents such as Triton X-100. In case of secretion in the cultured solution, the cultured mass is separated by known methods such as centrifugation to separate from microbial cells or cells, and the supernatant solution is collected.

The thus obtained human Serrate-2, which are contained in the cell extracts or cell supernatants, can be purified by known protein purification methods. During the purification process, for confirmation of existence of the protein, in case of the fused protein of the above FLAG and human IgGFc, it can be detected by immunoassay using antibody against known antigen epitope and can be purified. In case the fused protein is not expressed as such, the antibody against human Serrate-2 in Example 7 can be used for detection.

A more useful purification method is an affinity chromatography using antibody. Antibodies used in this case are antibodies described in Example 7. For fused protein, antibodies against other than human Serrate-2 are used, for example antibody against FLAG in the case of FLAG, and protein G or protein A in the case of human IgGFc as shown in Example 6.

Physiological functions of the thus purified human Serrate-2 protein or human Serrate-2 can be identified by various assay methods, for example, physiological activity assaying using cell lines and animals such as mice and rats, assay methods of intracellular signal transduction based on molecular biological means and binding with Notch receptor etc.

For that action, mainly an action suppressing cell differentiation will be expected, and actions such as stimulating tissue regeneration, etc. can be expected.

Namely, we have found that, as shown in Example 8, in the umbilical cord blood derived blood undifferentiated cells in which CD34 positive cell fraction is concentrated, polypeptides of the present invention have suppressive action of colony forming action against blood undifferentiated cells, which shows colony formation in the presence of cytokines.

Furthermore, as shown in Example 9, we have found that as a result of adding IgG1 chimera protein of human Serrate-2 to the liquid culture in the presence of cytokines, the human Serrate-2 had activities for significantly decreasing LTC-IC (Long-Term Culture-Initiating Cells) counts, which were positioned with most undifferentiated blood stem cells in the human blood undifferentiated cells.

These results indicate that the human Serrate-2 suppresses differentiation of blood undifferentiated cells, and these actions spread from blood stem cells to colony forming cells. Furthermore, pharmaceuticals containing the polypeptide of the present invention have action for protection and release of the bone marrow suppressive action, which is observed in adverse effects of antitumor agents.

Furthermore, as shown in example 10, we have studied on an action against vascular cells, for which an action of the molecules of the present invention has never been known except for blood cells, and found that the molecules of the present invention have an action to suppress growth of the human vascular endothelia cells. Consequently, the present invention includes growth suppressive agents for vascular cells and therapeutic agents for disease (refer to Folkman and Klagsbrun, SCIENCE 235, 442–447, 1987), which effect is expected by suppressing vascularization, containing polypeptides having amino acid sequence of SEQ ID NO: 1–3. The molecules of the present invention can be used for treatment of these diseases.

In pharmaceutical use, polypeptides of the present invention having above form is lyophilized with adding preferable stabilizing agents such as human serum albumin, and is used in dissolved or suspended condition with distilled water for injection when it is in use. For example, preparation for injection or infusion at the concentration of 0.1–1000 μg/ml may be provided. A mixture of the compound of the present invention 1 mg/ml and human serum albumine 5 mg/ml divided in a vial could maintain activity of the said compound for long term. For culturing and activating cells in vitro, lyophilized preparations or liquid preparations of the polypeptide of the present invention are prepared and are added to the medium or immobilized in the vessel for culture. Toxicity of the polypeptide of the present invention was tested. Any polypeptide, 10 mg/kg was administered intraperitoneally in mice, but no death of mice was observed.

In vitro physiological activity of the polypeptide of the present invention can be evaluated by administering to disease model mice or its resembled disease in rats or monkeys, and examining recovery of physical and physiological functions and abnormal findings. For example, in case of searching abnormality in relation to hemopoietic cells, bone marrow suppressive model mice are prepared by administering 5-FU series of antitumor agents, and bone marrow cell counts, peripheral blood cell counts and physiological functions are examined in the administered group or the non administered group of mice. Furthermore, in case of searching in vitro cultivation and growth of hemopoietic undifferentiated cells including hemopoietic stem cells, the bone marrow cells of mice are cultured in the groups with or without addition of the compound of the present invention, and the cell cultures are transferred into the lethal dose irradiated mice. Result of recovery is observed with the indications of survival rate and variation of blood counts. These results can be extrapolated to the humans, and accordingly useful effective data for evaluation of the pharmacological activities of the compound of the present invention can be obtained.

Applications of the compound of the present invention for pharmaceuticals include diseases with abnormal differentiation of cells, for example leukemia and malignant tumors. These are a cell therapy, which is performed by culturing human derived cells in vitro while maintaining their original functions or adding new functions, and a therapy, which is performed by regenerating without damage the functions originally existing in the tissues by administering the compound of the present invention under the regeneration after tissue injury. Amount of administration may differ in the type of preparation and ranges from 10 μg/kg to 10 mg/kg.

Further strong physiological activity can be achieved by expression forming a multimer of the polypeptide of the present invention. Human Serrate-2 having multimer structure can be produced by a method of expressing chimera protein with human IgG Fc region as described in the example and expressing the multimer having disulfide bond with hinge region of the antibody, or a method expressing chimera protein, in which antibody recognition region is expressed in the C-terminal or N-terminal, and reacting with the polypeptide containing extracellular part of the thus expressed said human Serrate and the antibody which recognize specifically the antibody recognition region in the C-terminal or N-terminal.

Among other methods, a method in which the fused protein bound with only the hinge region of the antibody is expressed and the dimer is formed by constructing with disulfide bond, can be mentioned. A multimer of human Serrate-2 having higher specific activity than the dimer can be obtained. The said multimer is constructed by fused protein which is prepared for expressing the peptide in the C-terminal, N-terminal or other region. The protein is prepared by forming a disulfide bond without affecting any ether activities of the human Serrate-2. The multimer structure can also be expressed by arranging one or more peptides containing SEQ ID NO: 1 or 2, with genetic engineering method in series or in parallel. Other known methods for providing multimer structure having dimer or more can be applied. Accordingly, the present invention includes any polypeptides containing SEQ ID NO: 1 or 2 in a dimer or higher structure prepared by genetic engineering techniques.

As another method, multimerization method using chemical cross-linker can be mentioned. For example, dimethylsuberimidate dihydrochloride for cross-linking lysine residue, N-(γ-maleimidebutyryloxy) succinimide for cross-linking thiol group of cysteine residue and glutaraldehyde for cross-linking between amino groups can be mentioned. A multimer with dimer or higher structure can be synthesized by applying these cross-linking reactions. Accordingly, the present invention includes any polypeptides containing SEQ ID NO: 1 or 2 in the form of dimer or higher structure prepared by chemical cross-linking agents.

In application of medical care in which cells are proliferated and activated in vitro and are returned to the body, human Serrate-2 of the form hereinabove can be added directly in the medium, but immobilization can also be made. Immobilization method includes applying amino group or carboxyl group in the human Serrate-2, using suitable spacers or the abovementioned cross-linkers, and the ligand can be covalently bound to the culture vessels. Accordingly, the present invention includes any polypeptides containing SEQ ID NO: 1 or 2 in the form existing on a solid surface. The human Serrate-2 molecule binds specifically with receptor, a Notch receptor molecule. For example, expression of Notch receptor can be detected by using fused protein with above extracellular region of the human Serrate-2 and human IgGFc. Notch is known to be involved in some types of leukemia (Elissen et al., Cell 66, 649–661, 1991). Accordingly, the polypeptides having SEQ ID NO:1 or 2 can be used for diagnostic reagents for in vitro or in vivo.

Antibody specifically recognizing the said human Serrate-2 can be prepared as shown in Example 7. Also it can be prepared by various methods described in the literature (Antibodies a laboratory manual, E. Harlow et al., Cold Spring Harbor Laboratory), and by recombinant antibody expressed in cells using immunoglobulin gene isolated by a method of gene cloning. These antibodies can be used for purification, detection and measurement of the human Serrate-2 of the present invention can be performed by using antibody, which specifically recognizes the humanSerrate-2 shown in Example 7, and can be applied as diagnostic agent for diseases such as malignant tumor accompanied with abnormal cell differentiation.

EXAMPLES

The following examples illustrate embodiments of the present invention, but are not to be construed as limiting.

Referential Example 1

Preparation of Human Serrate-1 Gene Probe

A mixed primer corresponding to amino acid sequence conserved in *Drosophila* Serrate and rat jagged, i.e. sense primer (SEQ ID NO: 8) and antisense primer (SEQ ID NO: 9), were used. The signals used in these sequence show each equivalent mixture: i.e. S: C and G, Y: T and C, W: T and A, K: G and T, R: A and G, N: C, G, T and A.

A synthetic oligonucleotide was prepared by using automatic DNA synthesizer with the principal immobilized method. The automatic DNA synthesizer used was 391PCR-MATE of Applied Biosystems Inc., U.S.A. Nucleotide, carrier immobilized with 3'-nucleotide, solution and reagents are used according to the instructions by the same corporation. Oligonucleotide was isolated from the carrier after finishing the designated coupling reaction and treating the oligonucleotide carrier, from which protective group of 5'-terminal was removed, with concentrated liquid ammonia at room temperature for one hour. For removing protective groups of nucleic acid and phosphoric acid, the reactant soluion containing nucleic acid was allowed to stand in the concentrated ammonium solution in the sealed vial at 55° C. for over 14 hours. Each oligonucleotide, from which the carrier and protective groups were removed, was purified by using OPC cartridge of the Applied Biosystems Inc., and detritylated by using 2% trifluoroacetic acid. Primer was dissolved in deionized water to set final concentration 100 pmol/μl after purification, and used for PCR. Synthesis of oligonucleotide was performed by the same manner.

Amplification by PCR was performed as follows.

Human fetal brain originated cDNA mixture solution (QUICK-Clone cDNA, CLONTECH Inc., U.S.A.) 1 μl was used. 10× buffer solution [500 mM KCl, 100 mM Tris-HCl (pH 8.3), 15 mM MgCl 2, 0.01% gelatin] 5 μl, dNTP Mixture (Takara Shuzo) 4 μl, sense primer DLTS1 (100 pmol/μl) 5 μl and antisense primer DLTA2 (100 pmol/μl) 5 μl which were specific to the above Serrate homologue and TaqDNA polymerase (AmpliTaq, Takara Shuzo., Japan, 5 U/μl) 0.2 μl were added thereto, and finally deionized water was added to set up total 50 μl. PCR was performed for 5 cycles of a cycle consisting of treatment at 95° C. for 45 seconds, at 42° C. for 45 seconds and 72° C. for 2 minutes, further 35 cycles of a cycle consisting of treatment at 95° C. for 45 seconds, at 50° C. for 45 seconds, and 72° C. for 2 minutes, and finally allowed to stand at 72° C. for 7 minutes. A part of the PCR products was subjected to 2% agarose gel electrophoresis, stained with ethidium bromide (Nippon Gene Co., Japan), and observed under ultraviolet light to confirm amplification of about 500 bp cDNA. The total amount of the thus obtained PCR product was subjected to electrophoresis with 2% agarose gel prepared with low melting point agarose (GIBCO BRL Inc., U.S.A.), stained with ethidium bromide, cutting out about 500 bp bands under the UV light, adding distilled water of the same volume as the gel, heating at 65° C. for 10 minutes, and completely dissolving the gel. The dissolved gel was centrifuged at 15000 rpm for 5 minutes to separate supernatant solution after adding an equal volume of TE saturated phenol (Nippon Gene Co., Japan) and the same separation operation was performed after adding TE saturated phenol:chloroform (1:1) solution and chloroform. DNA was recovered from the final solution by ethanol precipitation.

A vector, PCRII vector (Invitrogen Inc., U.S.A., hereinafter designated as pCRII) was used. The vector and the above DNA in a molar ratio of 1:3 were mixed and DNA was ligated into the vector by using T4 DNA ligase (Invitrogen Inc., U.S.A.). The pCRII, to which DNA was integrated, was subjected to gene transduction into *E. coli* one shot competent cells (Invitrogen Inc., U.S.A.) and was spread on the semi-solidmedium plate of L-Broth (Takara Shuzo Co., Japan) containing ampicillin (Sigma Corp., U.S.A.) 50 μg/ml and allowed to stand at 37° C. for about 12 hours. The visible colonies were randomly selected, inoculated in the L-Broth liquid medium 2 ml containing same concentration of ampicillin and shake cultured at 37° C. for about 18 hours. The cultured bacterial cells were recovered and the plasmid was separated by using Wizard Miniprep (Promega Inc., U.S.A.) according to the attached explanation sheet. The plasmid was digested by restriction enzyme EcoRI. Integration of the said PCR product was confirmed by incision of about 400 bp DNA. The base sequence of the incorporated DNA in the confirmed clone was determined by fluorescent DNA sequencer (Model 373S, Applied System Inc., U.S.A.). The gene cloning gene fragment was compared with amino acid sequence of Notch ligand molecule, i.e. *Drosophila* Serrate and rat Jagged, and significant analogous sequence was found, then the sequence was confirmed as cDNA fragment coding human Serrate-1.

Referential Example 2

Cloning of Full Length Human Serrate-1 Gene

A screening of clones having full length cDNA was performed by hybridization from human placenta origin cDNA library (inserted cDNA in λgt-11, CLONTEC Inc., U.S.A.) in plaques corresponding to 1×106 plaques. Generated plaques were transcribed to nylon filter (Hybond N+: Amersham Inc., U.S.A.). The transcribed nylon filter was subjected to alkaline treatment [allow to stand for 7 minutes on a filter paper permeated with a mixture of 1.5 M NaCl and 0.5 M NaOH], followed by twice neutralizing treatments [allow to stand for 3 minutes on a filter paper permeated with a mixture of 1.5 M NaCl, 0.5 M Tris-HCl (pH 7.2) and 1 mM EDTA]. Subsequently, the nylon filter was shaken for 5 minutes in 2-fold concentrated SSPE solution [0.36 M NaCl, 0.02 M sodium phosphate (pH 7.7) and 2 mM EDTA], washed, and air-dried. Then the nylon filter was allowed to stand for 20 minutes on a filter paper, which was permeated with 0.4 M NaOH, and was shaken for 5 minutes with 5-fold concentrated SSPE solution and was washed, then again air-dried. Screening was conducted in the human Serrate-1 probe labeled with radioisotope 3 2 P using the filter.

The DNA probe previously prepared was labeled with 3 2 P as follows. A DNA fragment was cut out by EcoRI from PCR II, to which purified PCR product by human Serrate primers (about 500 bp) was inserted and DNA fragments were isolated from low melting point agarose gel. The thus obtained DNA fragment was labeled by DNA labeling kit (Megaprime DNA labeling system: Amersham, U.S.A.) The primer solution 5 μl and deionized water were added to DNA 25 ng to set up total volume of 33 μl, which was treated for 5 minutes in boiling water bath. Reaction buffer solution 10 μl containingd NTP, α-3 2 P-dCTP 5 μl and T4 DNA polynucleotide kinase solution 2 μl were added thereto, and treated at 37° C. for 10 minutes in water bath. Subsequently, the mixture was purified by Sephadex column (Quick Spin Column Sephadex G-50: Boehringer Mannheim Inc., Germany), then treated for 5 minutes in boiling water bath and ice-cooled for 2 minutes for use.

Hybridization was performed as follows. The prepared filter hereinabove was immersed into prehybridization solution consisting of SSPE solution, in which final concentration of each component is set at 5-fold concentration, 5-fold concentration of Denhardt's solution (Wako Purechemicals), 0.5% SDS (sodium dodecyl sulfate) and salmon sperm (Sigma Co.) 10 μg/ml denatured by boiling (Sigma Co.) 10 μg/ml denatured by boiling water, shaken at 65° C. for 2 hours, then the filter was immersed into the hybridization solution, which was the same composition as the above prehybridization solution, containing the probe labeled with 3 2 P by the above mentioned method, and shaken at 55° C. for 16 hours to perform hybridization.

The filter was washed by immersing into SSPE solution containing 0.1% SDS, shaken at 55° C. twice, and further immersing into 10-fold dilution of SSPE solution containing 0.1% SDS four times at 55° C. The washed filter was treated with autoradiography using a sensitized screen. Clones of strongly exposed part were collected and plaques obtained were again spread and screened by the same method hereinbefore to separate a complete single clone.

The thus isolated phage clones were 22 clones. Phages of all of these clones was prepared to about 1×10 9 pfu, whereafter the phage DNA was purified, digested by restriction enzyme EcoRI and inserted into pBluescript (Stratagene Inc., U.S.A.), which was digested by EcoRI in the same way. DNA sequences of both ends of these clones were analyzed by DNA sequencer. Two clones of S16 and S20 were the clone containing DNA sequence from No. 1 to 1873 in the sequence listing, SEQ ID NO: 6. Clones S5 and S16 were the clone containing DNA sequence from No. 990 to 4005 in the sequence listing, SEQ ID NO: 6. The deletion mutant of these clones were prepared by using kilosequence deletion kit (Takara Shuzo Co.) according to a description of the attached paper. The full-length cDNA base sequence encoding a polypeptide of the present invention was determined using the DNA sequencer (Applied Biosystem Inc.) from both direction of 5'-direction and 3'-direction.

As a result, about 100 bp in an area coding C-terminal amino acid sequence were found to be not cloned, accordingly cloning of full-length gene was performed by using GIBCO-BRL, 3'RACE system kit according to the attached manual. Namely, cDNA cloning was performed by human origin poly A+RNA (CLONTECH Corp.) to 3'-direction and gene sequence was determined.

The thus cloned three gene fragments in a plasmid containing in a full-length DNA sequence of SEQ ID NO: 6 are inserted by applying restriction enzyme Bgl 2 site at DNA sequence No. 1293 in sequence ID NO: 6 and AccI site at No. 3943, between EcoRI and XbaI of multicloning site in pUC18 to prepare pUCSR-1. The sequence of this gene together with aminoacid sequence is shown in SEQ ID NO: 6.

Example 1

Preparation of Probe by PCR

Gene probes used for screening, i.e. gene described in SEQ ID NO: 10, 11 and 12, were obtained as follows. These sequences correspond to Genbank registered number, TO8853, R50026 and R45751. Hereinafter, a probe having gene sequence SEQ ID NO: 10 is designated as ¥1, a probe having gene sequence SEQ ID NO: 11 is designated as ¥2, and a probe having gene sequence SEQ ID NO: 12 is designated as ¥4.

Namely, a gene SEQ ID NO: 10 was isolated by PCR using primers of oligonucleotide having SEQ ID NO: 13 and 14; a gene SEQ ID NO: 11 was isolated by PCR using primers of oligonucleotide having SEQ ID NO: 15 and 16; and a gene SEQ ID NO: 12 was isolated by PCR using primers of oligonucleotide having SEQ ID NO: 17 and 18.

Amplification by PCR was performed as follows. Human fetal brain originated cDNA mixed solution (QUICK-Clone cDNA, CLONTECH Inc., U.S.A.) 1 μl was used. 10× buffer solution [500 mM KCl, 100 mM Tris-HCl (pH 8.3), 15 mM MgCl 2, 0.01% gelatin] 5 μl, dNTP mixture (Takara Shuzo Co., Japan) 4 μl, the primers hereinbefore (20 pmol/μl) each 1 μl, and TaqDNA polymerase (AmpliTaq, Takara Shuzo Co., 5 U/μl) 0.2 μl were added thereto, and finally deionized water was added to set up total 50 μl. PCR was performed for 40 cycles of a cycle consisting of treatment at 95° C. for 1 minute, at 55° C. for 5 minutes and 72° C. for 3 minutes, and finally allowed to stand at 72° C. for 7 minutes. A part of the PCR products was subjected to 2% agarose gel electrophoresis, stained with ethidium bromide (Nippon Gene Co., Japan), and observed under ultraviolet light to confirm amplification of objective size gene.

The total amount of the thus obtained PCR product was subjected to electrophoresis with 2% agarose gel prepared with low melting point agarose (GIBCO BRL Inc., U.S.A.), stained with ethidium bromide, cutting out each band under the UV light, adding distilled water of the equal volume of the gel, heating at 65° C. for 10 minutes, and completely dissolving the gel. The dissolved gel was centrifuged at 15000 rpm for 5 minutes to separate supernatant solution after adding equal volume of TE saturated phenol (Nippon Gene Co., Japan) and the same separation operation was performed after adding TE saturated phenol:chloroform (1:1) solution and chloroform. DNA was recovered from the final solution by ethanol precipitation.

A vector, PCRII vector (Invitrogen Inc., U.S.A., hereinafter designated as PCRII) was used. The vector and the above DNA in a molar ratio 1:3 were mixed and DNA was ligated into the vector by using T4 DNAligase (Invitrogen Inc., U.S.A.). The PCRII, to which DNA was integrated, was subjected to gene transduction in E. coli one shot competent cells (Invitrogen Inc., U.S.A.) and was spread on the semi-solid medium plate of L-Broth (Takara Shuzo Co., Japan) containing ampicillin (Sigma Corp., U.S.A.) 50 µg/ml and allowed to stand at 37° C. for about 12 hours. The visible colonies were randomly selected, inoculated in the L-Broth liquid medium 2 ml containing the same concentration of ampicillin, and shake cultured at 37° C. for about 18 hours. The cultured bacterial cells were recovered and the plasmid was separated by using Wizard Miniprep (Promega Inc., U.S.A.) according to the attached explanation sheet. The plasmid was digested by restriction enzyme EcoRI. Integration of the said PCR product was confirmed by incision of objective size DNA. The base sequence of the incorporated DNA in the confirmed clone was determined by fluorescent DNA sequencer (Model 373S3, Applied System Inc., U.S.A.). The sequence was compared with DNA sequence registered in Genbank hereinbefore. Isolation of gene having DNA sequences SEQ ID NO: 10, 11 and 12 was confirmed.

Example 2

Cloning of Full Length Human Serrate-2 Gene

A screening of clones having full length cDNA was performed by hybridization from human fetal brain origin cDNA library (inserted cDNA in λgt-11, CLONTECH Inc.) in plaques corresponding 1×10 6 plaques. Appeared plaques were fixed with alkali by the same method as described in Referential example 2. Using these filter and three types of probes, which were isolated in Example 1 and labeled with 3 2 P by the method described in Referential example 2, screening was performed on each individually to obtain clones.

Isolated phage clones were: 2 clones from a case using ¥1 as a probe; 6 clones from a case using ¥2 as a probe; and 4 clones from a case using ¥4 as a probe. Clones isolated by ¥4 were all included in clones isolated from ¥2. All of the phages of these clones were prepared to about 1×10 9 pfu, and phage DNA was purified by using Wizard Lambda preps (Promega Inc.) according to the attached explanation sheet, and digested by EcoRI, then incorporated into pBlusecript (Stratagene Inc.) or pUC18 (Pharmacia Inc.) digested by EcoRI.

The full DNA sequences of these clones were determined by DNA sequencer as same as Referential example 2, and a part of the identical sequence was compared. Result indicates that: #5 clone was a clone containing DNA sequence from No. 484 to 2025 in sequence ID NO: 4; #21 clone was a clone containing DNA sequence from No. 1882 to 3537 in SEQ ID NO: 4; and #86 clone was a clone containing DNA sequence from No. 2455 to 3955 in SEQ ID NO: 4. Remaining clones were those having only short insert consisting of a part identical with sequences of these clones. This result indicated that, as a result of comparison with amino acid sequences of human Serrate-1, the area encoding the N-terminal amino acid sequence was not cloned. Consequently, a probe having DNA sequence of SEQ ID NO: 19 was prepared and a screening of the second time was performed for cloning the cDNA in 5'-region. A probe was prepared as same as described in Example 1, namely PCR primers having DNA sequence of SEQ ID NO: 20 and 21 were subjected to PCR using #5 clone as a template. Library used was prepared as same as the first screening and conditions were performed by the same method as before.

The thus isolated clones in the second screening were six clones. Phages of all these clones were prepared about 1×10 9 pfu, purified by using Wizard Lambda Preps (Promega Inc.) according to the attached explanation sheet, digested by EcoRI and inserted into pUC 18 which was also digested with EcoRI. The full DNA sequences of these clones were determined by DNA sequence as same as in Referential example 2. As a result of comparison with a part of identical sequence, S43-1 clone was considered to contain the most 5'-direction. This clone was a clone containing DNA sequence from No. 38 to 1538 in SEQ ID NO: 4. The remaining clones have only short inserts consisting of a part identical with sequence determined already in the other clone or isolated in the first time.

Although a sequence of ATG, which codes translation initiation codon methionine, could not be found in the second screening clones, further cloning of cDNA sequence for 5'-direction was performed by 5'RACE method. 5' RACE was performed by using 5'RACE system kit (GIBCO-BRL Inc.) according to the attached manual. A cloning of cDNA with 5'-direction in the gene using human heart origin poly A+RNA (CLONTECH Inc.) was performed, and a gene sequence from DNA sequence No. 1 to No. 37 in SEQ ID NO: 4 was determined.

As a result, DNA sequence in SEQ ID NO: 4, i.e. cDNA sequence encoding full length of human Serrate-2, was determined.

In order to prepare cDNA encoding the full-length gene, and to obtain cDNA of the 5'-terminal, which could ligate with other clones, the following PCR was performed for cloning. Namely, using the oligonucleotide having DNA sequence in SEQ ID NO: 22 and the oligonucleotide having DNA sequence in SEQ ID NO: 23, PCR was performed using S43-1 clone as a template according to a method described in Example 1. Similarly, it was subcloned to pCRII and gene sequence was determined to prepare the clone having DNA sequence from No. 1 to No. 503 in SEQ ID NO: 4. This clone is designated as S2-5.

Among the above clones, i.e. gene S2-5, S43-1, #5, #21 and #86, S2-5 and S43-1 were applied in the restriction enzyme Spl I site at DNA sequence No. 217 in SEQ ID NO: 4; S43-1 and #5 were the same as in Kpn I site at No. 1453; #5 and #21 were the same as in Sac I site at No. 2016;and #21 and #86 were the same as in BamHI site at No. 2991, and finally DNA having DNA sequence SEQ ID NO: 4 was inserted between EcoRI site and Hind III site of multi cloning site of pUC 18 to prepare pUCSR-2.

Example 3

Expression of Human Serrate-2 in Organs

In order to examine expression of mRNA of human Serrate-2, using filters, which was previously transcribed with mRNA, i.e. Human Multiple Tissue Northern Blot, Human Multiple Tissue Northern Blot II, Human Multiple Tissue Northern Blot III and Human Fetal Multiple Tissue Northern-Blot II (CLONTECH Inc.), 3 2 P labeling was performed by the previous method using DNA labeling kit (Mega Prime DNA lebeling system: Amersham Inc.) hereinbefore mentioned, with a probe DNA having SEQ ID NO: 19 described in Example 2, and expression was examined with performing hybridization according to description of instruction for use attached to the above filters.

As a result, length of expressed mRNA was about 5 kb. Strong expressions in human adult tissues were observed in heart, skeletal muscle, thyroid gland, spinal cord and trachea; clear expression was observed in pancreas, prostate, testis, small intestine and adrenal gland, very weak expression was observed in brain, placenta, kidney, thymus, ovary, stomach and lymph node, and no expression was observed in lung, liver, spleen, colon, peripheral lympocytes and bone marrow. In the human fetal tissues, strong expression was observed in the fetal lung, clear expression: fetal brain and fetal kidney and no expression in fetal liver.

Example 4

Preparation of Expression Vector of Human Serrate-2

Using the gene consisting of DNA sequence described in the sequence listing, SEQ ID NO: 4, expression vectors of human Serrate-2 and its chimera protein mentioned in the following 1) to 5) were prepared.

1) Expression Vector of Secretory Extracellular Human Serrate-2

The cDNA coding polypeptide of amino acid sequence from No. 1 to 1055in the sequence listing, SEQ ID NO: 2 was ligated with expression vector pMKITNeo (Maruyama et al., Preliminary Paper, Japan Molecular Biology Soc. 1991, obtainable from Prof. Maruyama, Tokyo Medical and Dental Univ.), which has a SR α promoter and Neomycin resistant gene, to prepare expression vector.

Namely, vector pUCSR-2 containing DNA sequence in SEQ ID NO: 4 was used as template and oligonucleotide having sequence in SEQ ID NO: 26 and oligonucleotide having sequence in SEQ ID NO: 27 were used as primer, and PCR was performed according to a method described hereinbefore. The PCR product was ligated into cloning vector PCRII, whereupon the gene sequence of the PCR product was determined to prepare DNA having gene sequence from No. 2986 to 3254 of DNA sequence in SEQ ID NO: 4, in which termination codon and restriction enzyme Sal I site were attached in the 3' end.

About a 3 kbp gene fragment was obtained by digesting the pUCSR-2 with restriction enzyme EcoRI and BamHI, about a 250 bp gene fragment was obtained by digesting the pCRII vector with restriction BamHI and Sal I, the vector of which contained the above PCR product as an insert, and about a 4.3 kb gene fragment was obtained by digesting the pMKITNeo with restriction enzymes EcoRI and XhoI, and these 3 gene fragments were simultaneously ligated to obtain the expression vector containing gene fragment of DNA sequence from No. 1 to 3254 in SEQ ID NO: 4.

Secretory extracellular human Serrate-2 protein (hereinafter designated this protein as EXS2) expression vector pMEXS2 was obtained.

2) Expression Vector of FLAG Chimera Protein of Secretory Extracellular Human Serrate-2

The cDNA coding chimera protein, to which cDNA coding FLAG sequence (SEQ ID NO: 24) was added to the C-terminal of polypeptide from No. 1 to 1055 of amino acid sequence in the sequence listing, SEQ ID NO: 2 was ligated to the expression vector pMKINeo to prepare the expression vector.

Namely, vector pUCSR-2 containing DNA sequence in SEQ ID NO: 4 was used as template and oligonucleotide having sequence in SEQ ID NO: 26 and oligonucleotide having sequence in SEQ ID NO: 28 were used as primer, and PCR was performed according to a method described hereinbefore. The PCR product was ligated to cloning vector PCRII, and the gene sequence of the PCR product was determined to prepare DNA having gene sequence from No. 2986 to 3254 of DNA sequence in SEQ ID NO: 4, in which DNA sequence coding FLAG sequence in the 3' end (DNA sequence in SEQ ID NO: 24), termination codon and restriction enzyme Sal I site were attached in the 3'end.

About a 3 kbp gene fragment was obtained by digesting the pUCSR-2 with restriction enzyme EcoRI and BamHI, about a 300 bp gene fragment was obtained by digesting the pCRII vector with restriction enzymes BamHI and Sal I, the vector of which contained the above PCR product as an insert, and about a 4.3 kb gene fragment was obtained by digesting the pMKITneo with restriction enzymes EcoRI and XhoI, and these 3 gene fragments were simultaneously ligated (though recognition sequence of restriction enzymes Xho I and Sal I is different, they can be ligated due to complementary terminal gene sequence) to obtain the expression vector containing gene fragment of DNA sequence from No. 1 to 3254 in SEQ ID NO: 4 and gene fragment encoding FLAG sequence. Secretory extracellular human Serrate-2 FLAG chimera protein (hereinafter designated this protein as EXS2FLAG) expression vector pMEXS2FLAG was obtained.

3) Expression Vector of IgG1Fc Chimera Protein of Secretoruy Extracellular Human Serrate-2

A cDNA coding chimera protein, to which cDNA coding amino acid sequence of Fc region below the hinge part of human IgG1 was added to the C-terminal of polypeptide having amino acid sequence from No. 1 to 1055 of in the sequence listing, SEQ ID NO: 2, was ligated to the expression vector pMKINeo to prepare the expression vector. Peparation of fused protein with immunoglobulin Fc protein was performed according to the method of Zettlmeissl et al. (Zettlmeissl et al., DNA cell Biol., 9, 347–354, 1990). A gene using genome DNA with intron was applied and the said gene was prepared by using PCR.

Human genomic DNA was used as a template. Oligonucleotide of the sequence in the sequence listing, SEQ ID NO: 31 with restriction enzyme BamHI site, and oligonucleotide of the sequence in the sequence listing, SEQ ID NO: 32 with restriction enzyme XbaI site were used as primer. PCR of gene sequence encoding human IgG1F was performed using the primers and human genomic DNA as template. About 1.4 kbp band was purified, treated by restriction enzyme BamHI and XbaI (Takara Shuzo Co., Japan), and genes were ligated to pBluescript, which was similarly treated by restriction enzyme, by using T4 DNA ligase to prepare subcloning. Later, the plasmid DNA was purified and sequenced to confirm gene sequence, then the said gene sequence was confirmed as genome DNA in the hinge region of heavy chain of the human IgG1. (The sequence is referred to Kabat et al. Sequence of Immunological Interest, NIH Publication No. 91-3242, 1991). Hereinafter this plasmid is designated as pBShIgFc.

A vector pUCSR-2 having DNA sequence in SEQ ID NO: 4 was used as template and oligonucleotide having sequence in SEQ ID NO: 26 and oligonucleotide having sequence in SEQ ID NO: 29 were used as primer, and PCR was performed according to a method described hereinbefore. The PCR product was ligated to cloning vector pCRII, and the gene sequence of the PCR product was determined to prepare DNA having gene sequence from No. 2986 to 3254 of DNA sequence in SEQ ID NO: 4 in which restriction Bgl 2 site was attached in the 3' end.

About a 250 bp gene fragment was obtained by digesting the pCRII vector, which contained the above PCR product as an insert, with restriction enzymes EcoRI and BamHI containing a gene encoding the human IgG1FC as an insert were ligated. In this case, BamHI and Bgl 2 sites can be ligated due to complementary of the digested terminal gene sequence. Further this part cannot be digested by these restriction enzymes.

About a 1.5 kbp gene fragment was obtained by digesting this vector with restriction enzyme BamHI and Not 1, about a 3 kbp gene fragment was obtained by digesting PUCSR-2 with restriction enzymes EcoRI and BamHI, and about a 4.3 kb gene fragment was obtained by digesting pMKITneo with restriction enzyme EcoRI and Not 1, and these 3 gene fragments were simultaneously ligated (though restriction enzymes Xho I and Sal I have different recognition sequence, they can be ligated due to complementary terminal gene sequence). An expression vector containing gene fragment from DNA sequence No. 1 to 3254 in SEQ ID NO: 4 and a gene fragment coding human IgG1Fc, expression vector pMEXS2Fc of Ig chimera protein of secretory extracellular humanSerrate-2 (hereinafter this protein is designated as EXS2Fc), was obtained.

4) Expression Vector of Full Length Human Serrate-2 Protein

The cDNA coding polypeptide from No. 1 to 1212 of amino acid sequencein the sequence listing, SEQ ID NO: 3, was ligated to the expression vector pMKITNeo to prepare the expression vector.

Namely, about 4 kbp gene fragment, which was cut out by digesting pUCSR-2 with restriction enzymes EcoRI and Hind III, was ligated into pBluescript, which was digested with the same restriction enzymes. Subsequently, about 4 kbp gene fragment cut from this vector by digesting with EcoRI and XhoI was ligated with about 4.3 kb gene fragment obtained by digesting the expression vector pMKITneo with restriction enzymes EcoRI and Not 1 to prepare expression vector containing gene fragment of DNA sequence from No. 1 to 3955 in SEQ ID NO: 4. Full length human Serrate-2 protein (hereinafter this protein is designated as FS2) expression vector pMFS2 was obtained.

5) Expression Vector of FLAG Chimera Protein of Full Length Human Serrate-2

The cDNA coding chimera protein, to which cDNA coding FLAG sequence (SEQ ID NO: 24) was added to the C-terminal of polypeptide from No. 1 to 1212 of amino acid sequence in the sequence listing, SEQ ID NO: 3, was ligated to the expression vector pMKITNeo to prepare the expression vector.

Namely, vector pUCSR-2 having DNA sequence in SEQ ID NO: 4 was used as template and oligonucleotide having sequence in SEQ ID NO: 26 and oligonucleotide having sequence in SEQ ID NO: 30 were used as primer, and PCR was performed according to a method described hereinbefore. The PCR product was ligated to cloning vector pCRII, and the gene sequence of the PCR product was determined to prepare DNA having gene sequence from No. 2986 to 3725 of DNA sequence in SEQ ID NO: 4, in which DNA sequence coding FLAG sequence in the 3' end (DNA sequence in SEQ ID NO: 24), termination codon and restriction enzyme Sal I site were attached in the 3' end.

About a 3 kbp gene fragment was obtained by digesting the pUCSR-2 with restriction enzymes EcoRI and BamHI, about a 700 bp gene fragment was obtained by digesting the pCRII vector by restriction enzymes BamHI and SalI, the vector of which contained the above PCR product vector of which contained the above PCR product as an insert, and about a 4.3 kb gene fragment was obtained by digesting the pMKITneo with restriction enzymes EcoRI and XhoI, and these 3 gene fragments were simultaneously ligated (though recognition sequence of restriction enzymes XhoI and SalI is different, they can be ligated due to complementary terminal gene sequence) to obtain the expression vector containing gene fragment of DNA sequence from No. 1 to 3725 in SEQ ID NO: 4 and gene fragment coding FLAG sequence. Full length human Serrate-2 FLAG chimera protein (hereinafter designated this protein as FS2FLAG) expression vector pMFS2FLAG was obtained.

Example 5

Expression and Gene Transfer of the Human Serrate-2 Expression Vectors into Cells The expression vectors prepared in Example 4 were gene transduced into COS-7 cells (obtained from RIKEN Cell Bank, Physical and Chemical Research Institute, Japan, RCB0539).

Cell culture before transduction was performed by culturing in D-MEM (Dulbecco modified Eagle's medium, GIBCO-BRL Inc., U.S.A.) 10% FCS. On the day before gene transduction, medium of cells was changed to set cell counts 5×10 7 cells/ml and cultured overnight. On the day of gene transduction, cells were sedimented by centrifugation, centrifugally washed twice with PBS (−) and prepared to 1×10 7 cells/ml in PBS (−), 1 mM MgCl 2 and gene transfer was performed by electroporation using gene transduction device Gene-pulsar (Bio-Rad Inc., U.S.A.). The above cell suspension 500 μl was collected in the cell for electroporation (0.4 mm), expression vector 20 μg was added, and allowed to stand in ice for 5 minutes. Electroporation was performed under the condition 3 μF, 450V twice, and during the two electroporations the cell mixture was allowed to stand at room temperature for 1 minute. After 5 minutes in ice, cells were spread in the culture medium, diameter 10 cm previously added with 10 ml of the medium described hereinbefore, and cultured at 37° C. in 5% carbon dioxide incubator.

The next day, the culture supernatant solution was removed, the cells adhered to the dish were washed twice with PBS (−) 10 ml and serum-free D-MEM 10 ml was added and cultured for 4 days. In case of gene transduction into expression vectors pMEXS2, pMEXS2FLAG and pMEXS2Fc, culture supernatant solution was recovered and was replaced the buffer to PBS (−) by Centricon 30 (Amicon Inc., U.S.A.) and simultaneously the solution was concentrated to 10-fold to obtain cell culture supernatant solution.

In case of gene transduction of pMSF2 and pMFS2FLAG, after 4 days culture, cells were washed with PBS (−) 10 ml. Cells were scraped using cell scraper (Corster Corp.), PBS (−) 10 ml was added again, centrifuged at 1500 rpm for 5 minutes and washed. Cell precipitates were suspended in the cell lysis buffer [50 mM Hepes (pH 7.5), 1% Triton X-100, 10% glycerol, 4 mM EDTA, 50 µg/ml Aprotinin, 100 µM Leupeptin, 25 µM Pepstatin A and 1 mM PMSF] 500 µl, allowed to stand in ice for 20 minutes and centrifuged at 15000 rpm for 20 minutes to collect supernatant solution to obtain cell lysates.

Using these samples, expression of FLAG chimera and immunoglobulin chimera proteins were detected by Western blotting. Namely, concentrated cultured supernatants or cell lysates were subjectd to SDS-PAGE using an electrophoresis tank and polyacrylamide gel for SDS-PAGE (gradient gel 5–15%) (ACI Japan Inc.) according to manufacturer's construction. Samples were prepared by treatment in boiling water for 5 minutes with 2-mercapto-ethanol (2-ME) for reduction, and non-reduced condition without taking the above treatment. As a marker, Rainbow Marker (high molecular weight, Amersham Inc.) was used. Sample buffer solution and electrophoresis buffer were prepared with reference to the attached leaflet. When the SDS-PAGE was finished, acrylamide gel was transcribed to PVDF membrane filter (BioRad Inc., U.S.A.) using the Mini Trans Blot Cell (BioRad Inc.).

The thus prepared filter was shaken overnight at 4° C. in Blockace (Dainippon Pharm. Co., Japan), TBS-T [20 mM Tris, 137 mM NaCl (pH 7.6) and 0.1% Tween 20] to effect blocking. According to the explanation of the attached leaflet of ELC Western blotting detection system (Amersham Inc., U.S.A.); in case that protein was FLAG chimera, anti-FLAG M2 mouse monoclonal antibody (Eastman Kodak, U.S.A.) was used as primary antibody, and peroxidase labeled anti-mouse Ig sheep antibodies (Amersham Inc., U.S.A.) as a secondary antibody, were reacted. In case of human IgG1Fc chimera, peroxidase labeled anti-human Ig sheep antibodies (Amersham Inc., U.S.A.) were reacted. Reaction time for antibodies was 1 hour at room temperature, and at an interval of each reaction, washing was performed by shaking in TBS-T at room temperature for 10 minutes for three times. After the final washing, the filter was immersed in the reaction solution of ELC-Western blotting detection system (Amersham Inc., U.S.A.) for 1 minute, and wrapped in polyvinylidene chloride wrap for exposure to X-ray film.

As a result, the bands showing protein obtained by transduction of expression vector pMEXS2FLAG were detected from COS supernatant about 135 kD by anti-FLAGM2 antibody; and production of objective protein EXS2FLAG was confirmed, and transduced cells by expression vector pMEXS2FLAG. Molecular weight changes depending on reduction treatment at the SDS-PAGE were not observed. About 20 kD of sugar chains was added to the molecules as a result of comparing with a molecular weight estimated by amino acid sequence.

Furthermore, a band having molecular weight about 165 kD was detected from supernatant solution of COS cells, to which the expression vector pMEXS2Fc was gene transduced, on SDS-PAGE by anti-human Ig sheep antibody under reducing conditions. A band having molecular weight about 330 kD was detected under non-reducing conditions. These results indicated that objective protein EXS2Fc was produced, and consequently transformed cells by the expression vector pMEXS2Fc could be obtained. As the molecular weight of EXS2Fc under reducing conditions is about half of that under non-reducing conditions, the EXS2Fc is estimated to have a construction of dimer through disulfide bond. Furthermore, the molecular weight of the band is about 40 kD larger than that calculated from amino acid sequence. This indicates addition of sugar chain to the molecule.

Furthermore, a band having molecular weight about 150 kD was detected from extract of COS cells, to which the expression vector pMFS2FLAG was gene transduced, on SDS-PAGE by anti-FLAG M2 antibody under reducing conditions. The results indicated that the objective protein FS2FLAG was produced, and consequently cells transformed by expression vector pMFS2FLAG, were obtained. As the molecular weight of FS2FLAG of the band is about 20 kD larger than that calculated by amino acid sequence, sugar chains may be added to the extracellular region.

As for a protein other than chimera protein, detection was conducted by using anti-human Serrate-2 mouse monoclonal antibody and anti-human Serrate-2 rabbit polyclonal antibody, which were described in Example 7, as primary antibodies in the Western blotting. Also as secondary antibody, anti-mouse Ig sheep antibody (Amersham Inc.) or peroxidase labeled rabbit Ig sheep antibody (Amersham Inc.) were used.

As a result, a band having molecular weight about 135 kD was detected in the supernatant of COS cells, to which the expression vector pMEXS2 wasgene transduced. This indicated that objective protein EXS2 was produced, and cells transformed by an expression vector pMEXS2 could be obtained. No changes of molecular weight were observed caused by reduction treatment on SDS-PAGE. A band having molecular weight about 150 kD was detected under reducing conditions from COS cell extract, to which the expression vector pMFS2 was gene transduced. These results indicated that objective protein FS2 was produced, and consequently cells transformed by the expression vector pMFS2 could be obtained. Furthermore, in every case, molecular weight of the band is about 20 kD larger than that calculated from amino acid sequence. This indicates addition of sugar chains to the molecule of the extracellualr region.

In the control experiments, cell lysate and cultured supernatant solution of COS-7 cells, to which pMKITNeo vector was transformed, were tested. No bands reacted with anti-FLAG antibody, anti-human Ig antibody or anti-human Serrate-2 antibody could be detected.

Example 6

Purification of Secretory Extracellular Human Serrate-2 Chimera Proteins of Gene Transduction Cells Cultured supernatant of COS-7 cells transformed by the expression vector pMEXS2FLAG or pMEXS2Fc by a method in Example 5, were prepared in large scale, and chimera protein, i.e. EXS2FLAG or EXS2Fc, was purified by affinity column chromatography.

In case of EXS2FLAG, 2 liters of the cultured supernatant obtained by the method in Example 5 was passed through a column packed with Anti-FLAG M2 Affinity Gel (Eastman Kodak, U.S.A.). The chimera protein was absorbed in a column by a reaction of affinity of anti-FLAG antibody of the gel and FLAG sequence of the chimera protein. An inner diameter 10 mm, disposable column (BioRad Inc., U.S.A.) was used with packing the above gel 5 ml. A circulation system consisting of medium bottle→column→peristaltic pump→medium bottle was set up. The circulation was run by a flow 1 ml/min. for 72 hours. Thereafter the column was washed with PBS (−) 35 ml and eluted by 0.5 M Tris-glycine (pH 3.0) 50 ml. The eluate of 25 fractions, each 2 ml, was collected into the tube (Farcon Inc. 2063), and each fraction was neutralized by 200 µl of 0.5 M Tris-HCl (pH 9.5) previously added in each tube.

The eluate fraction, each 10 µl of the EXS2FLAG which was purified by the above method was subjected to reduction treatment described in Example 5. SDS-PAGE electrophoresis by 5–10% gradient polyacrylamide gel was performed. After finishing the electrophoresis, silver staining was conducted by using Wako silver stain kit II according to the explanation of the attached leaflet. Fractions from No. 4 to 8 showed detectable bands in EXS2FLAG. The size is identical with the result of Western blotting of anti-FLAG antibody obtained in Example 5. Therefore, purified EXS2FLAG was obtained.

In the EXS2Fc, two liters of the cultured supernatant solution was absorbed in Protein A Sepharose column (Pharmacia Inc., Sweden) according to the same method as above to collect the eluate fractions. Using a part of eluate as same as in EXS2FLAG, a determination of the eluate fraction, identification of the size and detection of the purity were performed by SDS-PAGE electrophoresis and silver staining in reducing conditions. Therefore, the eluate fractions from No. 4 to 15 were detected as bands. The molecular weight thereof is identical with the result of Example 5. Therefore, purified EXS2Fc was obtained.

Example 7

Preparation of Antibodies Recognizing Human Serrate-2

EXS2FLAG, purified by the method in Example 6, was used as immunogen, and rabbits were immunized. After assaying antibody titer, whole blood was collected and serum was obtained. Anti-human Serrate-2 rabbit polyclonal antibody were purified by using Econopack serum IgG purification kit (BioRad Inc., U.S.A.) with reference to the attached explanation leaflet.

EXS2FLAG purified by a method described in Example 6 was used as immunogens, and mouse monoclonal antibodies were prepared according to the explanation of the textbook. The purified HSFLAG was administered in Balb/c mice (Nippon SLC Co., Japan), 10 µg/mouse, immunized intracutaneously and subcutaneously. After second immunization, increased serum titer was confirmed by collecting blood ophthalmologically, and the third immunization was performed. Subsequently, the spleen of mice was collected and fused with mouse myeloma cells P3X63Ag8 (ATCC TIB9) using polyethyleneglycol. Hybridoma was selected by HAT medium (Immunological and Biological Research Institute, Japan), and the hybridoma strains, which produced antibody specifically recognizing extracellular region of human Serrate in the medium, were isolated by enzyme immunoassay. The hybridoma strains producing mouse monoclonal antibody, which specifically recognized human Serrate-2, were established.

Anti-human Serrate-2 monoclonal antibody was purified and prepared by using Mab Traq GII (Pharmacia Inc., Sweden) and according to the explanation of the leaflet, from the supernatant of the thus established hybridoma.

Affinity column chromatography was performed by using the monoclonal antibody. Preparation of the affinity column was performed according to the explanation attached to the CNBr activated Sephadex 4B (Pharmacia Inc., Sweden). Coupling efficiency was 99.6%. A column, 2 cm×1 cm, containing gel 2 ml, was prepared.

A supernatant of the cultured cells, which contained EXS2, was passed through the column. The supernatant solution was passed at 20 ml/hr, subsequently PBS (−) 15 ml was passed at the same flow rate and washed the column. Finally, the products were eluted by a mixture of 0.1 M sodium acetate and 0.5 M NaCl (pH 4.0). The eluate, each 1 ml fraction was collected, and was neutralized by adding 1 M Tris-HCl (pH 9.1) 200 µl for each fraction.

SDS-PAGE of purified protein was conducted under reducing conditions according to the method described in Example 5, followed by silver staining and Western blotting to estimate molecular weight. A band of about 140 kD was detected. Consequently, Western blotting can be made by using the said monoclonal antibodies and human Serrate-2 can be purified by the affinity columns.

Example 8

Effects of Human Serrate-2 Protein on Colony Formation of Blood Undifferentiated Cells In order to observe physiological action of human Serrate-2 on blood undifferentiated cells, CD34 positive cells were cultured in a serum-free semi solid medium in the presence of EXS2Fc and known cytokines, and the number of colony forming cells were observed.

CD34 positive cells of human umbilical cord blood or human normal bone marrow blood were isolated from the mononuclear cells, which were treated by silica solution (Immunological and Biological Research Institute, Japan) according to the attached explanation leaflet and fractionated from the low density cellular fraction (<1.077 g/ml) by densitometric centrifugation of Ficoll pack (Pharmacia Inc., Sweden).

Separation of CD34 positive cells was performed by using Dynabeads M-45 CD34 or DETACH a BEADS CD34 (Dynal Inc., Norway) and according to the attached explanation leaflets. After separation, the purity was measured as follows. Cells were stained by FITC labeled CD34 antibody HPCA2 (Beckton-Deckinson Inc., U.S.A.) and examined by flow-cytometer (FACS Calibur, Beckton-Deckinson., U.S.A.). Purity above 85% was confirmed for use.

The thus isolated CD34 positive cells were suspended homogeneously to form 400 cells/ml of the medium hereinbelow, and spread in a 35 mm dish (Falcon Inc., U.S.A.), then cultured for 2 weeks in a carbon dioxide incubator at 37° C. under 5% carbon dioxide, 5% oxygen, 90% nitrogen and 100% humidity. The formed blood colonies were counted under an invert microscope.

A medium used is α-medium (GIBCO-BRL Inc., U.S.A.), containing 2% deionized bovine serum albumin (BSA, Sigma, U.S.A.), 10 µg/ml human insulin (Sigma, U.S.A.), 200 µg/ml transferring (Sigma, U.S.A.), 10–5 M 2-mercaptoethanol (Nakarai Tesk Co., Japan), 160 µg/ml soybean lecithin (Sigma, U.S.A.), 96 µg/ml cholesterol (Sigma, U.S.A.) and 0.9% methylcellulose (Wako Pure Chemicals, Japan).

To the above medium, under the following conditions of cytokines, human Serrate-2 extracellular Ig chimera protein (EXS2Fc) was added to the final concentration of 1 µg/ml. For control, human IgG1 (Athens Research and Technology Inc., U.S.A.) was added with the same concentration in order to observe the effect of IgGFc region.

Conditions of cytokines are as follows. 100 ng/ml human SCF, 10 ng/ml human IL-3, 100 ng/ml human IL-6, 2 U/ml Epo (Chugai Seiyaku Co., Japan) and 10 ng/ml human G-CSF (Chugai Seiyaku Co., Japan).

Results are shown in Table 1. Number of colonies/400 CD34+ cells are shown in mean of n=3. Four different origin human umbilical cord blood CD34 positive cells were used.

TABLE 1

|  | EXS2Fc not added | EXS2Fc added |
|---|---|---|
| Experiment 1 | 30.1 | 12.8 |
| Experiment 2 | 48.3. | 40.7 |
| Experiment 3 | 38.2. | 28.1 |
| Experiment 4 | 50.9. | 37.1 |

As shown in Table 1, the human Serrate-2 has an action against four different origin umbilical cord blood CD34 positive cells. Therefore, human Serrate-2 of the present invention has suppressive action for differentiation of blood undifferentiated cells including blood cells.

Example 9

Effect of Human Serrate-2 on Blood Undifferentiated Cell LTC-IC in Liquid Culture In order to observe physiological action of human Serrate-2 on the blood undifferentiated cells, umbilical cord blood positive cells were cultured for two weeks in the serum-free liquid medium in the presence of EXS2Fc and known cytokines, and the numbers of LTC-IC, which was thought to represent most undifferentiated cells at present, were observed.

The umbilical cord blood mononuclear CD34 positive cells, 100000 to 20000 cells, separated by a method described in Example 8 were cultured in the following medium for 2 weeks. Numbers of LTC-IC in 3 experimental groups, which include a group before cultivation, a group of EXS2Fc and a control group, were determined.

Media used in liquid culture medium were α-medium with 2% BSA added thereto, 10 μg/ml human insulin, 200 μg/ml transferrin, 40 μg/ml low density lipoprotein, 10-5 M 2-mercaptoethanol, further containing 100 ng/ml human SCF, 10 ng/ml human IL-3, and 100 ng/ml IL-6. EXS2Fc 1 μg/ml was added 1 the above medium. In the control group, human IgG1 was added in the equal concentration.

Preparation of human bone marrow stromal cell layer used for LTC-IC, and quantitative assay of frequency of LTC-IC by a limit dilution were performed according to a method of Sutherland et al. (Blood, 74, 1563-, 1989 and Proc. Natl. Acad. Sci. USA, 87, 3584-, 1990).

The bone marrow mononuclear cells, 1–2×10 7 cells, obtained in Example 8 before the separation and without the liquid silica treatment, were cultured in LTC medium (MyceloCult, Stem Cell Technologies Inc., Canada) 5 ml containing hydrocortisone 1 μM (Upjohn Japan Co., Japan) in T-25 flask (Falcon Inc., U.S.A.) at 37° C. under 5% carbon dioxide and 100% humidity in the carbon dioxide incubator. Culture was conducted until the adhesive cell layers of the stromal cell formation spread more than 80% of the bottom area of the culture flask. Detachment of the cell layer was performed by treating with EDTA solution (Cosmobio Co., Japan). Cells were plated in the 96 well plate (Beckton-Deckinson Inc., U.S.A.), about 2×10 4 cells/well and re-cultivation was continued in the same medium. X-ray, 15 Gy, 250 KV peak was irradiated to the reconstituted stromal cell layer. Growth of stromal cells was stopped and blood cells in the stromal cells were removed. The thus prepared stromal cells were used as stromal cell layer for the experiments.

In the assay of LTC-IC, cell counts in each group were adjusted within the ranges of 25–400 cells/well for CD34 positive cells before the cultivation, and 625–20000 cells/well for the cells after the cultivation, and cells were diluted for a six step-dilution within these ranges. Each dilution step of cells was cocultured with the above stromal cell layer in the 96 well plate, for 16 wells of one dilution step. Culture was performed in the same medium as used in stromal formation, at 37° C., 5% carbon dioxide and 100% humidity in the carbon dioxide gas incubator for 5 weeks. Cells in suspension and in attachment after cultivation were recovered in each well. Collected cells were transferred to the semi-solid culture medium consisting of α-medium containing 0.9% methylcellulose, 30% fetal calf serum (FCS, ICN Biochemical Japan), 1% BSA, 10-5 M 2-mercaptoethanol, 100 ng/ml human SCF, 10 ng/ml human IL-3, 100 ng/ml human IL-6, 2 U/ml Epo and 10 ng/ml human G-CSF. After 2 weeks of cultivation, colony forming cells were detected in the same way as described in Example 8, and numbers of wells in which colony forming cells were found, were detected. Incidence of LTC-IC was calculated according to the method of Taswell et al. (J. Immunol. 126, 1614-, 1981) based on the above data. Results are shown in Table 2.

TABLE 2

| Before cultivation | | EXS2Fc not added | EXS2Fc added |
|---|---|---|---|
| Total number of cells | 19475 | 1210000 | 930000 |
| Number of LTC-IC | 185 | 23 | 5 |

From the results shown in Table 2, human Serrate-2 has an action against LTC-IC and reduces its number.

Example 10

Effect of Human Serrate-2 on Growth of Vascular Endothelial Cells

The vascular endothelial cells used were passage cultures of four generations of normal human aortic endothelial cells and normal human pulmonary arterial endothelial cells (Kurabo Inc., Japan). Cells were plated 500 cells/well in 96 well plate for tissue culture (Falcon Inc., U.S.A.) in the tertiary passage culture, and cultured in a medium with low serum level for growth of vascular endothelial cells (HuMedia-EG2, Kurabo Inc., Japan) containing human recombinant EGF (KuraboInc., Japan) 100 ng/ml and human recombinant EGF-B 5 ng/ml. Human Serrate-2 extracellular chimera protein (EXS2Fc) was added to the final concentration of 1 μg/ml. For control, human IgG1 (Athens Research and Technology Inc., U.S.A.) was added with the same concentration in order to observe effect of IgGFc region. A control experiment was conducted without adding protein except for HuMedia-EG2. Culture was performed at 37° C., under 5% carbon dioxide and 100% humidity for 3 days and the number of cells was calculated.

Vascular endothelial cell counts were performed by using NR reagent set (Kurabo Inc., Japan). The method was developed by Borenfeund and Puerner (Journal of Tissue Culture Methods, 9(1), 7–9, 1984), i.e. the neutral red method which applied that vital stain pigment neutral red (3-amino-7-dimetylamino-2-methylphenazine hydrochloride) passed through plasma membrane of living cells and was accumulated in lysosome.

Absorption at 540 nm was measured by using immuno reader (NJ-2000, Japan Intermed Inc., Japan).

Results showed that in case of aortic endothelial cells, absorption in the control group was at an optical density (OD) 0.21±0.02, which is almost the same level of human IgG1 added group 0.20±0.01, and in EXS2Fc containing group, it was 0.10±0.02 which was significantly smaller than the control.

In case of pulmonary arterial endothelial cells, the control group showed 0.15±0.01 and the human IgG1 containing group showed almost same level 0.16±0.02, whereas EXS2Fc added group shows significantly low level of 0.07±0.02. This result indicated that EXS2Fc suppresses growth of vascular endothelial cells.

Human Serrate-2 of the present invention therefore has an action for regulating differentiation of undifferentiated cells, and can be used as a novel regulating agent for differentiation of cells.

The invention claimed is:

1. A method for suppressing differentiation of undifferentiated cells, comprising contacting said cells with an isolated polypeptide comprising SEQ ID NO:2.

2. A method for suppressing differentiation of undifferentiated cells, comprising contacting said cells with an isolated polypeptide comprising SEQ ID NO:3.

3. The method according to claim 1, wherein the undifferentiated cells are other than those of brain and nervous system or muscular system cells.

4. The method according to claim 2, wherein the undifferentiated cells are other than those of brain or nervous system or muscular system cells.

5. The method according to claim 1, wherein the undifferentiated cells are undifferentiated blood cells.

6. The method according to claim 2, wherein the undifferentiated cells are undifferentiated blood cells.

7. A method for suppressing proliferation of vascular endothelial cells, comprising contacting said cells with an isolated polypeptide comprising SEQ ID NO:2.

8. A method for suppressing proliferation of vascular endothelial cells, comprising contacting said cells with an isolated polypeptide comprising SEQ ID NO:3.

9. A method for suppressing differentiation of undifferentiated cells comprising contacting said cells with an isolated polypeptide comprising of SEQ ID NO:1.

10. The method according to claim 9 wherein the undifferentiated cells are undifferentiated cells other than those of brain and nervous system or muscular system cells.

11. The method according to claim 9 wherein the undifferentiated cells are undifferentiated blood cells.

12. A method for suppressing proliferation of vascular cells, comprising contacting said cells with an isolated polypeptide comprising SEQ ID NO:1.

* * * * *